US011565009B2

(12) United States Patent
Kim et al.

(10) Patent No.: US 11,565,009 B2
(45) Date of Patent: Jan. 31, 2023

(54) DISPLAY APPARATUS AND CONTROL METHOD THEREOF

(71) Applicant: SAMSUNG ELECTRONICS CO., LTD., Suwon-si (KR)

(72) Inventors: Hyungsuk Kim, Suwon-si (KR); Dasom Park, Suwon-si (KR); Dayoung Lee, Suwon-si (KR); Hanbin Lee, Suwon-si (KR); Seungwoo Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 181 days.

(21) Appl. No.: 16/942,199

(22) Filed: Jul. 29, 2020

(65) Prior Publication Data

US 2021/0052756 A1    Feb. 25, 2021

(30) Foreign Application Priority Data

Aug. 22, 2019    (KR) .................. 10-2019-0103017

(51) Int. Cl.
*A61L 2/10*    (2006.01)
*F21K 9/69*    (2016.01)
(Continued)

(52) U.S. Cl.
CPC .................. *A61L 2/10* (2013.01); *F21K 9/69* (2016.08); *F21V 33/0052* (2013.01);
(Continued)

(58) Field of Classification Search
CPC .... A61L 2/10; A61L 2202/11; A61L 2202/14; A61L 2202/16; F21K 9/69;
(Continued)

(56) References Cited

U.S. PATENT DOCUMENTS 9,233,179 B2 *    1/2016    Ranta .................... G06F 1/1607
9,912,790 B2 *    3/2018    Kim .......................... A61L 2/10
(Continued)

FOREIGN PATENT DOCUMENTS

JP            2018-7929 A      1/2018
KR    10-2010-0113743 A     10/2010
(Continued)

OTHER PUBLICATIONS

Communication dated Nov. 20, 2020, issued by the International Searching Authority in counterpart International Application No. PCT/KR2020/009777 (PCT/ISA210).
Communication dated Jan. 14, 2021, issued by the European Patent Office in counterpart European Application No. 20187310.6.
Communication dated Nov. 8, 2022 by the European Patent Office for European Patent Application No. 20187310.6.

*Primary Examiner* — Bao Q Truong
(74) *Attorney, Agent, or Firm* — Sughrue Mion, PLLC

(57) ABSTRACT

A display apparatus, including a display panel; a touch sensor provided on the display panel and configured to detect a user touch input; an ultraviolet (UV) light source provided on an edge portion of the display panel and configured to emit UV light to the display panel from the edge portion of the display panel; and a controller electrically connected to the display panel, the touch sensor, and the UV light source, wherein the controller is configured to, based on a determination that the user touch input is not detected, control the UV light source to emit the UV light toward the display panel.

20 Claims, 30 Drawing Sheets

(51) Int. Cl.
*F21V 33/00* (2006.01)
*G06F 1/16* (2006.01)
*G06F 3/041* (2006.01)
*F21Y 115/10* (2016.01)

(52) U.S. Cl.
CPC .......... *G06F 1/1607* (2013.01); *G06F 3/0412* (2013.01); *G06F 3/0416* (2013.01); *A61L 2202/11* (2013.01); *A61L 2202/14* (2013.01); *A61L 2202/16* (2013.01); *F21Y 2115/10* (2016.08)

(58) Field of Classification Search
CPC .. F21V 33/0052; G06F 1/1607; G06F 3/0412; G06F 3/0416; F21Y 2115/10
See application file for complete search history.

(56) References Cited

U.S. PATENT DOCUMENTS

| | | |
|---|---|---|
| 2011/0256019 A1 | 10/2011 | Gruen et al. |
| 2011/0291995 A1 | 12/2011 | Shr et al. |
| 2015/0258228 A1 | 9/2015 | Cohen et al. |

FOREIGN PATENT DOCUMENTS

| | | |
|---|---|---|
| KR | 10-1813077 B1 | 12/2017 |
| KR | 10-2018-0016003 A | 2/2018 |
| WO | 2013/081672 A1 | 6/2013 |
| WO | 2015/051024 A1 | 4/2015 |

* cited by examiner

FIG. 1
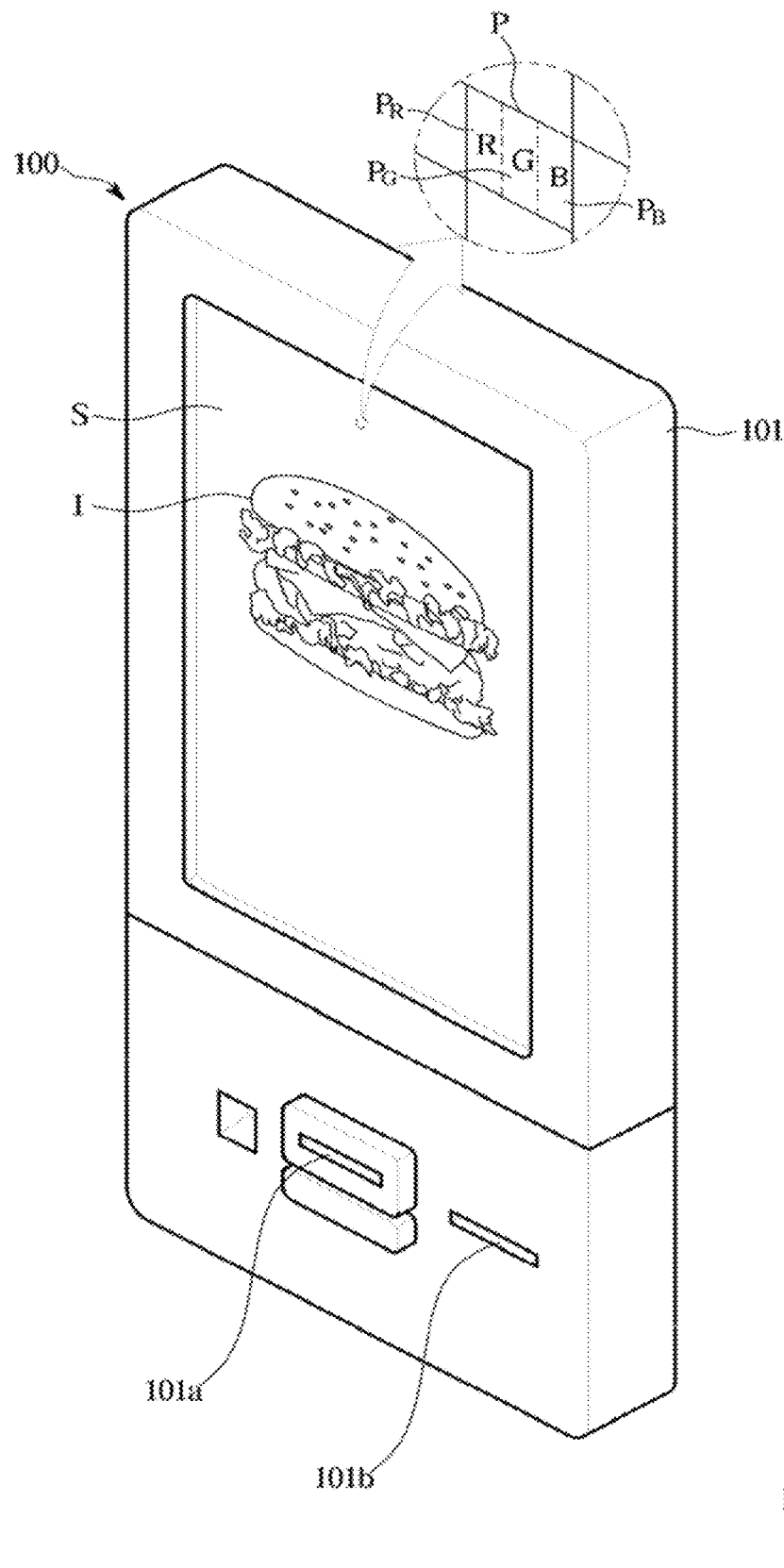
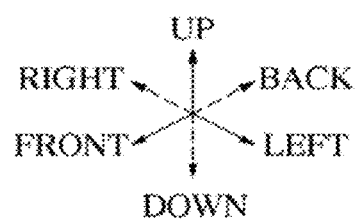

DISPLAY APPARATUS AND CONTROL METHOD THEREOF

CROSS-REFERENCE TO RELATED APPLICATION (S)

This application is based on and claims priority under 35 U.S.C. § 119 to Korean Patent Application No. 10-2019-0103017, filed on Aug. 22, 2019, in the Korean Intellectual Property Office, the disclosure of which is incorporated by reference herein in its entirety.

BACKGROUND

1. Field

The disclosure relates to a display apparatus and a control method thereof, and more particularly to a display including a touch screen and a control method thereof.

2. Description of the Related Art

Generally, a display apparatus may be an output apparatus that visually displays obtained or stored image information to a user, and is used in various fields such as home or workplace.

A display apparatus may be combined with a touch panel configured to detect a user touch, and interact with the user. For example, a kiosk corresponding to an interactive kiosk may be installed at the workplace, provide information about a product sold at the workplace to a user, and sell a product through user interaction.

The display apparatus configured to detect a user touch may be contaminated by bacteria or the like, because a large number of the public may use the display apparatus.

SUMMARY

Provided is a display apparatus capable of sterilizing a surface of a display in contact with a user body, and a control method thereof.

Provided is a display apparatus capable of emitting ultraviolet light on a surface of a display without a user being exposed to ultraviolet light, and a control method thereof.

Additional aspects of the disclosure will be set forth in part in the description which follows and, in part, will be obvious from the description, or may be learned by practice of the disclosure.

In accordance with an aspect of the disclosure, a display apparatus includes a display panel; a touch sensor provided on the display panel and configured to detect a user touch input; an ultraviolet (UV) light source provided on an edge portion of the display panel and configured to emit UV light to the display panel from the edge portion of the display panel; and a controller configured to, based on no user touch input being detected for a reference amount of time, control the UV light source to emit the UV light toward the display panel.

The touch sensor may further include: an infrared light source provided on a first edge portion of the display panel and configured to emit infrared light, and an infrared sensor provided on a second edge portion of the display panel and configured to detect the infrared light.

The UV light source may further include a plurality of UV light emitting diodes (UV LEDs) provided on the edge portion of the display panel.

Each of the plurality of UV LEDs may further include: an LED chip configured to emit the UV light; and a lens configured to refract the UV light emitted from the LED chip, wherein the lens has a cylindrical shape, and wherein one end of the cylindrical shape has a substantially hemispherical shape.

A central axis of the lens may be inclined to face the display panel.

Each of the plurality of UV LEDs may further include: an LED chip configured to emit the UV light; and a lens configured to refract the UV light emitted from the LED chip, wherein the lens has a cylindrical shape having a bevel that is substantially oblique.

A central axis of the lens may be substantially parallel to a surface of the display panel and, wherein the bevel of the lens faces the display panel.

The controller may be further configured to control the UV light source to emit the UV light toward the display panel based on a touch input for terminating a service.

The controller may be further configured to control the UV light source to emit the UV light toward the display panel based on a determination that the user touch input is not detected for the reference amount of time after receiving a touch input for terminating a service.

The controller may be further configured to control the UV light source to emit the UV light toward the display panel based on a touch input for terminating a service while a current time is within a predetermined sterilization time slot.

The controller may be further configured to control the UV light source to emit the UV light toward the display panel based on a touch input allowing sterilization of the display panel.

The controller may be further configured to control the UV light source to emit the UV light toward a touch position corresponding to the user touch input.

The controller may be further configured to determine a number of times that the user touch input is received, and to control the UV light source to emit the UV light toward the display panel based on whether the number is equal to or greater than a reference number.

The controller may be further configured to control the UV light source to emit the UV light toward the display panel for an amount of time that determined based on a number of times that the user touch input is received.

In accordance with an aspect of the disclosure, a control method for a display apparatus comprising a touch sensitive display includes displaying an image on the touch sensitive display; detecting a user touch on the touch sensitive display; based on no user touch being detected for a reference amount of time, emitting ultraviolet light toward the touch sensitive display; and displaying a predetermined image on the touch sensitive display while emitting the ultraviolet light.

The ultraviolet light may be emitted toward the touch sensitive display based on a touch input for terminating a service.

The ultraviolet light may be emitted toward the touch sensitive display based on a determination that the user touch is not detected by the touch sensitive display for the reference time after receiving a touch input for terminating a service.

The ultraviolet light may be emitted toward the touch sensitive display based on a touch input for terminating a service while a current time is within a predetermined sterilization time slot.

The ultraviolet light may be emitted toward a touch position of the user touch.

The ultraviolet light may be emitted toward the touch sensitive display based on whether a number of times that the user touch is received is equal to or greater than a reference number.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 1 is a view illustrating an exterior of a display apparatus according to an embodiment;

DETAILED DESCRIPTION

Figure 2:
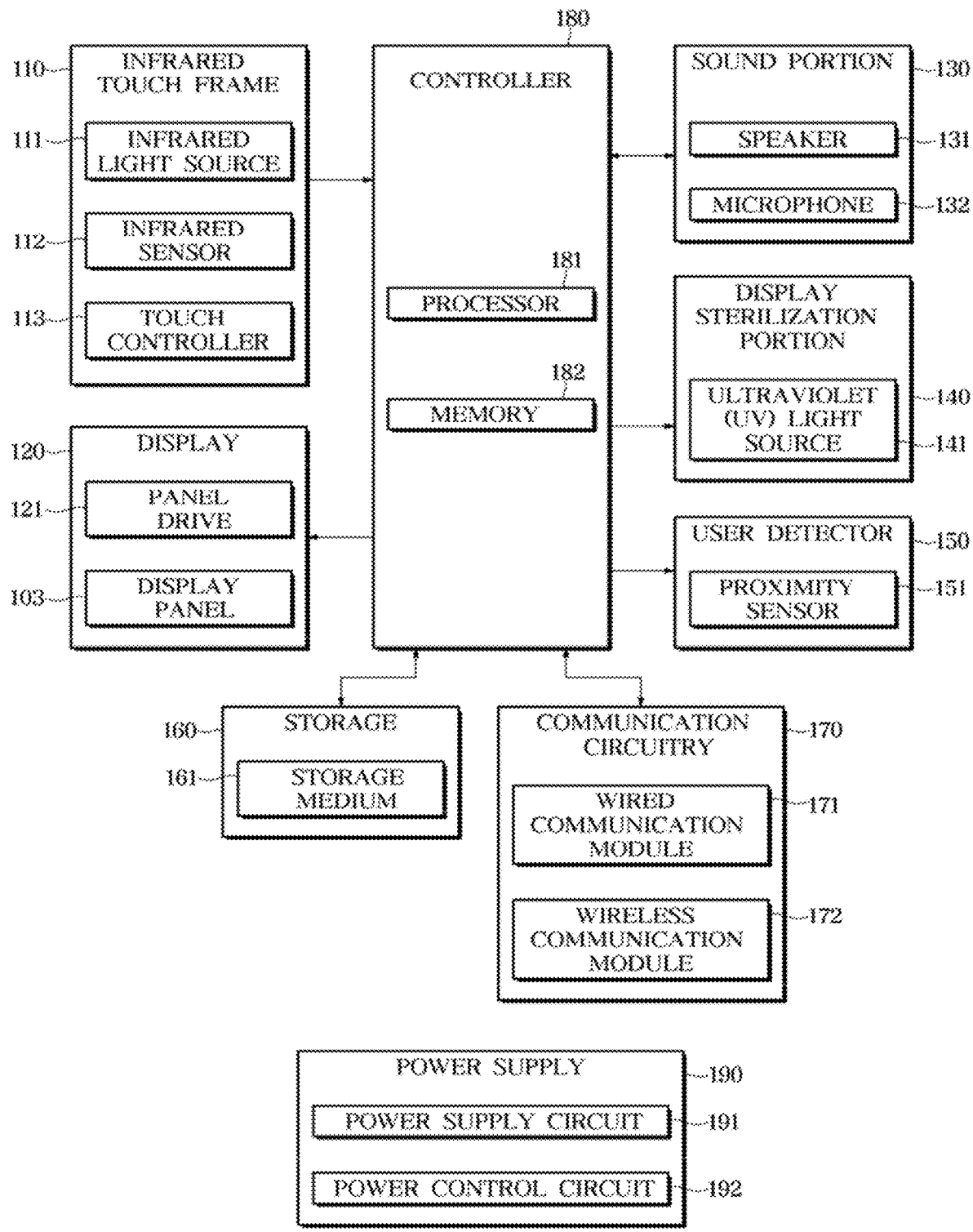
FIG. 2 is a diagram illustrating a control configuration of the display apparatus according to an embodiment.

The following detailed description is provided to assist in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed, with the exception of operations necessarily occurring in a particular order. In addition, respective descriptions of well-known functions and constructions may be omitted for increased clarity and brevity.

Embodiments will be described more fully hereinafter with reference to the accompanying drawings. The embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. Like numerals generally denote like elements throughout.

It will be understood that, although the terms first, second, etc. may be used herein to describe various elements, these elements should not be limited by these terms. These terms are only used to distinguish one element from another. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present.

The terminology used herein is for the purpose of describing particular embodiments only and is not intended to be limiting. As used herein, the singular forms "a," "an," and "the," are intended to include the plural forms as well, unless the context clearly indicates otherwise.

Reference will now be made in detail to embodiments of the present disclosure, examples of which are illustrated in the accompanying drawings, wherein like reference numerals generally refer to like elements throughout.

The expression, "at least one of a, b, and c," should be understood as including only a, only b, only c, both a and b, both a and c, both b and c, or all of a, b, and c.

FIG. 1 is a view illustrating an exterior of a display apparatus according to an embodiment.

A display apparatus 100 may be a device that processes an image signal received from the outside and visually displays the processed image. Hereinafter a case in which the display apparatus 100 is an interactive kiosk (hereinafter referred to as 'kiosk') is described, but the disclosure is not limited thereto. For example, the display apparatus 100 may be implemented in various forms such as a monitor, a portable multimedia device, a portable communication device, and a portable computing device, and the display apparatus 100 is not limited in its shape as long as visually displaying an image.

The display apparatus 100 may be installed indoors in locations such as subway stations, shopping malls, movie theaters, companies, and stores. Further, the display apparatus 100 may be installed outdoors in locations such as a roof of a building or a bus stop. That is, the display apparatus 100 may be installed in any place where there is a large number of the public.

The display apparatus 100 may receive a video signal and an audio signal from various content sources, and output video and audio corresponding to the video signal and the audio signal. For example, the display apparatus 100 may receive television broadcast content through a broadcast reception antenna or cable, receive content from a content playback device, or receive content from a content providing server of a content provider.

The display apparatus 100 may detect approach of a body part of a user, for example, hand and finger, or contact of a body part of the user, which may hereinafter be referred to as "touch". For example, the user may touch a display of the display apparatus 100, and the display apparatus 100 may identify/determine the location or coordinate, at which the user touch occurred on the display. At this time, the display may display an image inducing a user command or a user selection, for example, an image indicating "yes" and/or "no". The display apparatus 100 may identify or determine a user command or a user selection, which may hereinafter be referred to as "touch input", based on an image inducing the user command or the user selection, and a location that the user touches on the display.

As illustrated in FIG. 1, the display apparatus 100 may include a body 101 in which a plurality of components for displaying an image is placed, and a screen S provided on one side of the body 101 to display an image I.

The body 101 may form an appearance of the display apparatus 100, and the body 101 may include a component configured to allow the display apparatus 100 to display the image I. Although the body 101 illustrated in FIG. 1 is in the form of a flat plate, the shape of the body 101 is not limited thereto. For example, the body 101 may have a shape in which the left and right ends protrude forward and the central portion is curved so as to be concave.

The screen S may be formed on the front surface of the body 101, and the image I corresponding to visual information may be displayed on the screen S. For example, on the screen S, a still image or a moving image may be displayed and further, a two-dimensional plane image or a three-dimensional image may be displayed.

A plurality of pixels P may be formed on the screen S and the image I displayed on the screen S may be formed by a combination of the light emitted from the plurality of pixels P. For example, a single still image may be formed on the screen S by combining light emitted from the plurality of pixels P as a mosaic.

Each of the plurality of pixels P may emit different brightness and different color of light.

Each of the plurality of pixels P may include a plurality of point light sources, for example, organic light emitting diodes, configured to directly emit light, or a plurality of shutters, for example, a liquid crystal panel, configured to transmit or block light emitted from a surface light source such as a backlight unit.

The plurality of pixels P may include sub-pixels Pr, Pg, and Pb. The sub-pixels may include a red sub pixel Pr configured to emit a red light R, a green sub pixel Pg configured to emit a green light G, and a blue sub pixel Pb configured to emit a blue light B. For example, the red light may represent a light beam having a wavelength of approximately 620 nanometers (nm), wherein one nm refers to one billionth of a meter, to 750 nm, the green light may represent a light beam having a wavelength of approximately 495 nm to 570 nm, and the blue light may represent a light beam having a wavelength of approximately 450 nm to 495 nm.

A touch sensor configured to detect a user touch may be provided on the screen S or an edge portion of the screen S.

The touch sensor may include an infrared touch frame or a capacitive touch panel or a resistive touch panel. The infrared touch frame may be provided at the edge portion of the screen S and detect a user touch by detecting light blocked by a body part of a user. The capacitive touch panel may be provided on the screen S, and detect a user touch by detecting a change in the capacitance due to the user contact or approach. The resistive touch panel may also be provided on the screen S and detect a user touch by detecting a pressure caused by user contact.

For example, when the display apparatus 100 is a kiosk as illustrated in FIG. 1, a card slot 101a configured to allow a user to pay for a product after the user purchases the product, and a receipt slot 101b configured to issue a receipt in response to purchase of the product by a user may be provided under the screen S.

Figure 3:
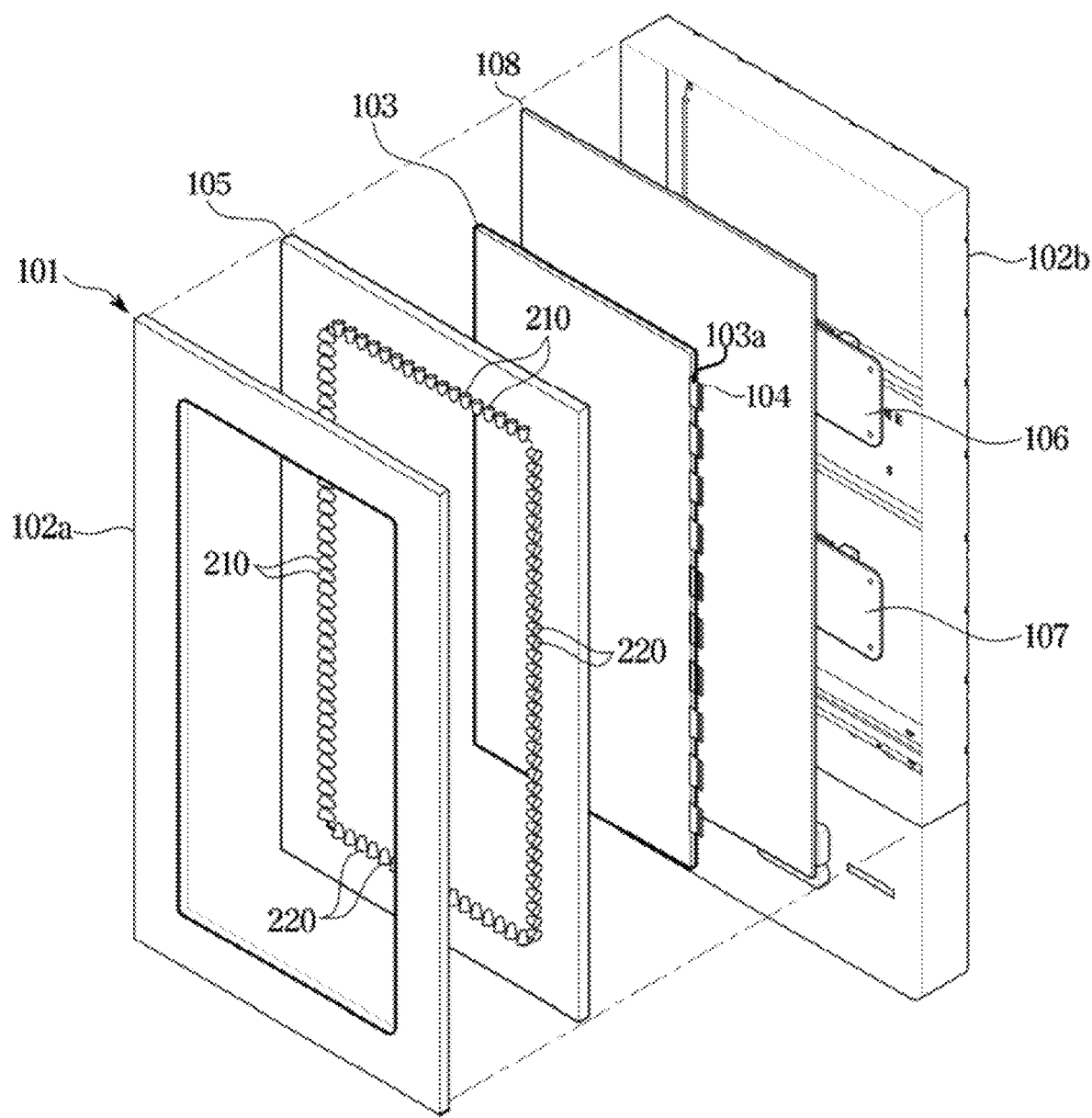
FIG. 3 is an exploded view illustrating the display apparatus according to an embodiment.
Figure 4:
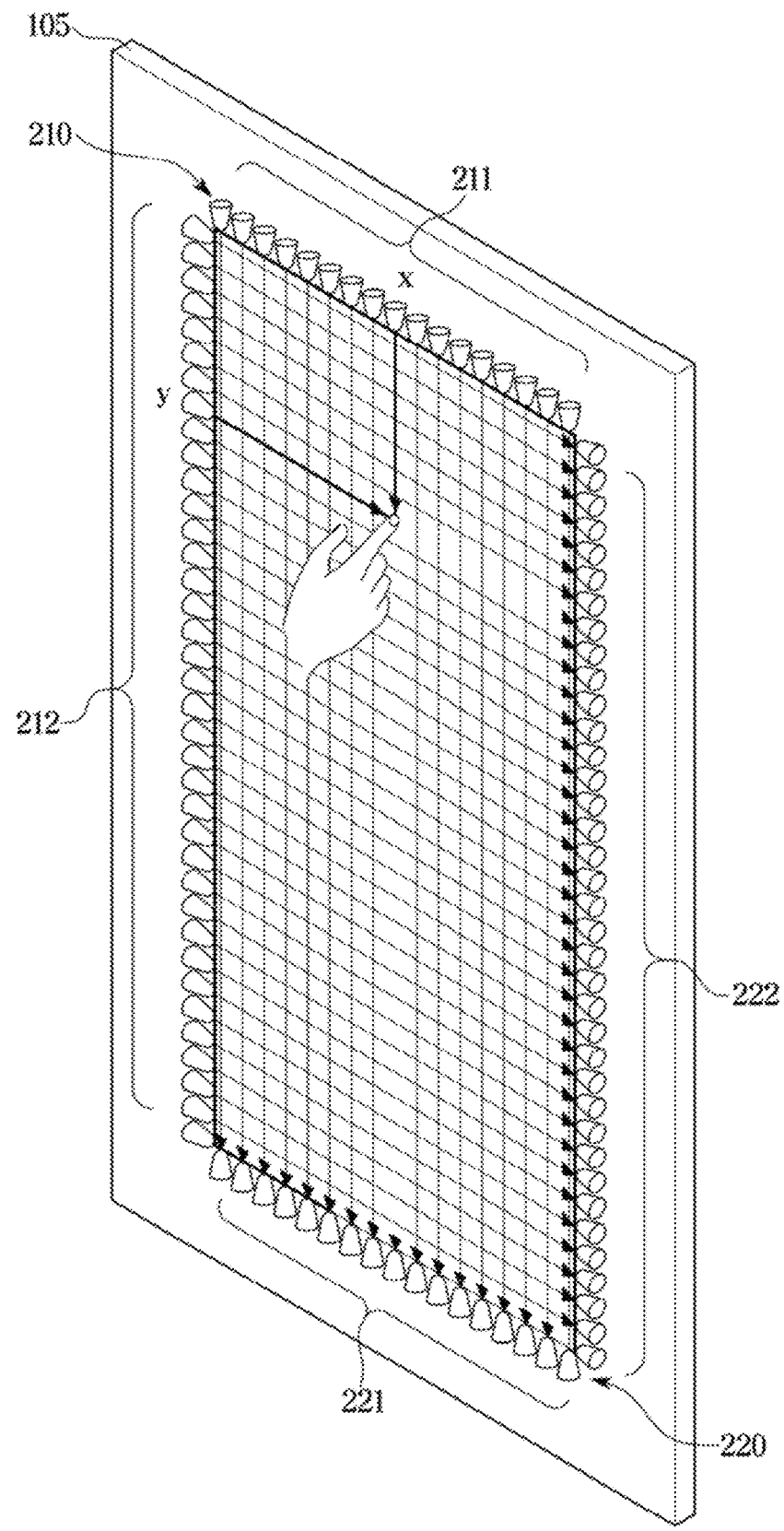
FIG. 4 is view illustrating an infrared touch frame included in the display apparatus according to an embodiment.
Figure 5:
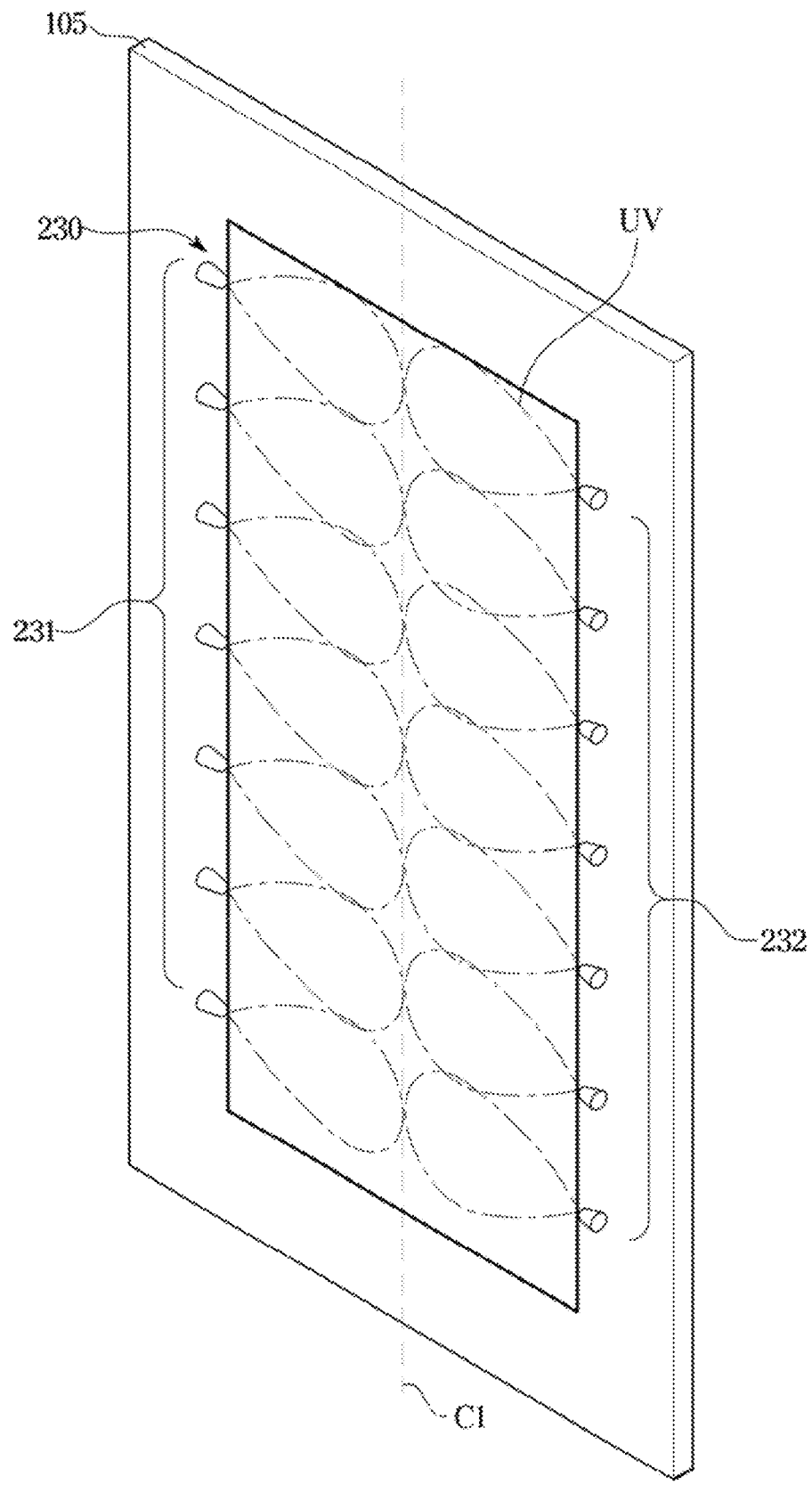
FIG. 5 is a view illustrating a plurality of ultraviolet (UV) light sources included in the display apparatus according to an embodiment.

FIG. 2 is a diagram illustrating a control configuration of the display apparatus according to an embodiment. FIG. 3 is an exploded view of the display apparatus according to an embodiment. FIG. 4 is view illustrating an infrared touch frame included in the display apparatus according to an embodiment. FIG. 5 is a view illustrating a plurality of ultraviolet (UV) light sources included in the display apparatus according to an embodiment.

Various components for displaying an image I on the screen S and detecting a user touch may be provided inside the body 101. The body 101 may include a housing 102b accommodating various configurations included in the display apparatus 100 described below.

Referring to FIGS. 2 to 5, the display apparatus 100 may include an infrared touch frame 110 configured to receive a touch input from a user, a display 120 configured to display an image, a sound portion 130 configured to receive and output sound, a display sterilization portion 140 configured to sterilize a surface of the display 120, a user detector 150 configured to detect user approach, a storage 160 configured store image data, a communication circuitry 170 configured to receive image data from an external device, a controller 180 configured to process content data received from the storage 160 and/or the communication circuitry 170, and a power supply 190 configured to supply power to a variety of component of the display apparatus 100.

The infrared touch frame 110 may include an infrared light source 111, an infrared sensor 112, a touch controller 113, and a front frame 105.

The infrared light source 111 may transmit infrared light. For example, the infrared light source 111 may include a plurality of infrared light emitting diodes (IR LEDs) 210.

The plurality of IR LEDs 210 may emit infrared light and may be installed on the front frame 105 provided at the edge portion of the screen S as illustrated in FIG. 3.

For example, the plurality of IR LEDs 210 may include m first IR LEDs 211 installed on an upper portion of the front frame 105, for example an upper edge portion of the screen S, and n second IR LEDs 212 installed on a left portion of the front frame 105, for example a left edge portion of the screen S. In this example, "m" and "n" may represent natural numbers.

The m first IR LEDs 211 may emit infrared light toward the lower portion of the screen S in response to a control signal of the touch controller 113, respectively, and the n second IR LEDs 212 may emit infrared light toward the right side of the screen S in response to the control signal of the touch controller 113, respectively.

However, the infrared light source 111 is not limited to including an IR LED. Therefore, the infrared light source 111 may include an infrared lamp configured to emit infrared light.

Each of the infrared sensors 112 may detect infrared light and output electrical signals in response to the detected infrared light. For example, the infrared sensor 112 may include a plurality of infrared ray (IR) photodiodes 220.

The plurality of IR photodiodes 220 may detect infrared light and output electrical signals, and may be installed on the front frame 105 provided at the edge portion of the screen S as illustrated in FIG. 3.

For example, as illustrated in FIG. 4, the plurality of IR photodiodes 220 may include m first IR photodiodes 221 installed on a lower portion of the front frame 105, for example a lower edge portion of the screen S, and n second IR photodiodes 222 installed on a right portion of the front frame 105, for example a right edge portion of the screen S.

The m first IR photodiodes 221 each may detect infrared light from the upper portion of the screen S and transmit an electrical detection signal, which depends on whether or not the infrared light is detected and/or detection intensity of infrared light, to the touch controller 113. The second IR photodiodes 222 each may detect infrared light from the left side of the screen S and transmit an electrical detection signal, which depends on whether or not the infrared light is detected and/or detection intensity of infrared light, to the touch controller 113.

The touch controller 113 may allow the plurality of IR LEDs 210 to emit infrared light, and determine a user touch position (touch coordinates) based on a detection signal received from the plurality of IR photodiodes 220.

For example, as illustrated in FIG. 4, the first IR LEDs 211 and the second IR LEDs 212 emit infrared light, and the first IR photodiodes 221 and the second IR photodiodes 222 may detect infrared light. At this time, when a user touches a first point (x, y) of the screen S, an x-th first IR photodiode from the left edge, among the first IR photodiodes and a y-th second IR photodiode from the upper edge, among the second IR photodiodes may not detect the infrared light. The touch controller 113 may determine a user touch position (touch coordinates) based on the detection signal of the x-th first IR photodiode and the y-th second IR photodiode.

The touch controller 113 may transmit touch data indicating a user touch position to the controller 180.

The front frame 105, in which the plurality of IR LEDs 210 and the plurality of IR photodiodes 220 are installed, may be fixed to a front bezel 102a provided in front of the display apparatus 100. In addition, the plurality of IR LEDs 210, the plurality of IR photodiodes 220 and the front frame 105 may be protected from the outside by the front bezel 102a.

The display 120 may include a display panel 103 configured to visually display an image and a panel drive 121 configured to drive the display panel 103.

In response to an analog image signal received from the panel drive 121, the display panel 103 may emit light and display an image.

The front surface of the display panel 103, which may be the surface from which light is emitted, may form the screen S of the display apparatus 100 described above.

The pixels P or sub-pixels Pr, Pg, and Pb described above may be formed on the display panel 103. Each of the pixels P may receive an electrical signal corresponding to an image from the panel drive 121 and output light corresponding to the received electrical signal. Accordingly, one image may be displayed on the display panel 103 by combining light output from the plurality of pixels P.

The display panel 103 may include a self-luminous display panel in which each of the plurality of pixels P emits light by itself and a non-self-luminous display panel in which each of the plurality of pixels P transmits or blocks light emitted from the backlight unit. For example, the display panel 103 may include a liquid crystal display (LCD) panel, an inorganic light emitting diode (LED) panel, or an organic light emitting diode (OLED) panel.

The panel drive 121 may receive digital image data from the controller 180 and allow the display panel 103 to display an image corresponding to the received image data. The panel drive 121 may transmit an analog image signal to each of the plurality of pixels P included in the display panel 103.

The panel drive 121 may include a display driver integrated circuit (DDI) 104, which may be referred to as a "driver IC", installed in the vicinity of the display panel 103 and configured to process digital image data so as to output a an analog image signal.

As illustrated in FIG. 3, a cable 103a configured to transmit image data to the display panel 103 may be provided on one side of the display panel 103 and the driver IC 104 may be provided on the cable 103a.

The cable 103a may electrically connect the display panel 103 to the driver IC 104, and may also electrically connect the driver IC 104 to the controller 180. The cable 103a may include a flexible flat cable or a film cable.

The driver IC 104 may receive digital image data from the controller 180 through the cable 103a, and may transmit analog image data to the display panel 103 through the cable 103a.

Further, the cable 103a and the driver IC 104 may be integrally implemented such as a film cable, chip on film (COF), or tape carrier packet (TCP). In other words, the driver IC 104 may be disposed on the cable 103a. However, the position of the driver IC is not limited thereto, and thus the driver IC 104 may be disposed on the display panel 103, or the driver IC 104 may be integrally formed with the controller 180.

The sound portion 130 may include a speaker 131 configured to acoustically output a sound and a microphone 132 configured to receive an external sound signal.

The speaker 131 may convert an analog sound signal output from the controller 180 into sound, for example a sound wave. For example, the speaker 131 may include a membrane and a coil configured to vibrate the membrane according to an analog sound signal. Sound waves may be generated by vibration of the membrane.

The microphone 132 may receive sound from the outside or voice, which may be for example a sound wave, uttered from the user. The microphone 132 may convert the received sound wave into an analog sound signal. For example, the microphone 132 may include a membrane vibrated by sound waves and a coil configured to generate an analog sound signal through the vibration of the membrane. The analog sound signal generated by the coil may be provided to the controller 180.

The display sterilization portion 140 may include an ultraviolet (UV) light source 141.

The UV light source 141 may emit ultraviolet light. Ultraviolet light may refer to light having a shorter wavelength than a purple light on the electromagnetic spectrum, and ultraviolet light may be not visible to the human eye. The wavelength of ultraviolet light may be longer than visible light and shorter than X-ray. For example, ultraviolet light may have a wavelength range from approximately 10 nm to 400 nm.

Ultraviolet light may be classified into ultraviolet light A (UV-A), ultraviolet light B (UV-B), and ultraviolet light C (UV-C) according to the wavelength. UV-A may have a wavelength range from approximately 315 nm to 400 nm, and UV-B may have a wavelength range from approximately 280 nm to 315 nm. UV-C may have a wavelength range from approximately 100 nm to 280 nm.

Ultraviolet light may cause interactions in molecules within the body as well as simply heating organisms. Ultraviolet light may destroy biological tissues, and even microorganisms such as bacteria. For this reason, ultraviolet light is widely used for sterilization purposes. UV-C may have the strongest sterilizing power among UV-A, UV-B and UV-C.

The display sterilization portion 140 may sterilize the surface of the display panel 103 by emitting ultraviolet light generated by the UV light source 141 to the display panel 103.

The display apparatus 100, for example a kiosk, used for the sale of a product may be touched by various users, and the surface of the display apparatus 100 may be contaminated by various bacteria by the user touch. Particularly, the display panel 103 configured to receive the user touch input may be easily contaminated by bacteria. In addition, bacteria on the display panel 103 may contaminate a body part of another user, for example a hand.

In order to prevent the contamination of the display panel 103 by the bacteria, the display sterilization portion 140 may emit ultraviolet light having a sterilizing effect, particularly ultraviolet light in the UV-C wavelength range, to the surface of the display panel 103.

The UV light source 141 may include a plurality of ultraviolet ray light emitting diodes (UV LEDs) 230.

The plurality of UV LEDs 230 may emit ultraviolet light, and may be installed on the front frame 105 provided at the edge portion of the screen S as illustrated in FIG. 3.

For example, the plurality of UV LEDs 230 may include p first UV LEDs 231 installed on a left portion, for example a left edge portion of the screen S, of the front frame 105 and p second UV LEDs 232 installed on a right portion of the front frame 105, for example a right edge portion of the screen S, as illustrated in FIG. 5. In this example, "p" may represent a natural number.

The p first UV LEDs 231 may emit ultraviolet light to a center line C1 passing through from an approximate upper center of the screen S to an approximate lower center of the screen S. Further, The p second UV LEDs 232 may also emit ultraviolet light to the center line C1.

An intensity of ultraviolet light emitted from the first UV LEDs 231 may be adjusted and thus ultraviolet light may reach the center line C1 of the screen S or more from the left edge of the screen S. Particularly, the intensity of ultraviolet light emitted from the first UV LEDs 231 may be adjusted to sterilize approximately 99% of bacteria in a range from the left edge of the screen S to the center line C1 of the screen S within a predetermined time, for example, 5 seconds. A magnitude of a current supplied to the first UV LEDs 231 may be adjusted to control the intensity of ultraviolet light emitted from the first UV LEDs 231.

A magnitude of a current supplied to the second UV LEDs 232 may also be adjusted for the same reason as the first UV LEDs 231.

The first UV LEDs 231 may be disposed at regular distances to each other. The distance between the first UV LEDs 231 may be adjusted according to the intensity of ultraviolet light emitted from the first UV LEDs 231. For example, in the range of the first UV LEDs 231, the distance may be determined to sterilize approximately 99% of the bacteria within the predetermined time, for example, 5 seconds.

A distance between the second UV LEDs 232 may also be adjusted for the same reason as the first UV LEDs 231.

Therefore, as illustrated in FIG. 5, the plurality of UV LEDs 230 may sterilize approximately 99% of bacteria in the entire surface area of the display panel 103 within the predetermined time, for example, 5 seconds.

However, the plurality of UV LEDs 230 is not limited to being installed on opposite edges of the display 120. For example, the plurality of UV LEDs 230 may be installed on the upper edge and the lower edge of the display 120. The plurality of UV LEDs 230 may be installed on any one of the upper edge, lower edge, left edge, and right edge of the display 120, or may be installed on all of them. In other words, the plurality of UV LEDs 230 may be installed on at least one of an upper edge, a lower edge, a left edge, and a right edge of the display 120.

Examples of the arrangement of the plurality of UV LEDs 230 are described in more detail below.

However, the UV light source 141 is not limited to including an UV LED. Therefore, the UV light source 141 may include a mercury lamp or black light configured to emit ultraviolet light.

The user detector 150 may include a proximity sensor 151 configured to detect an object positioned in front of the display apparatus 100 such as a user.

For example, the proximity sensor 151 may include an infrared sensor. The infrared sensor may detect infrared light emitted from the human body, and may transmit an infrared detection signal indicating whether or not infrared light is detected, to the controller 180. The controller 180 may determine whether or not the user approaches the display apparatus 100 based on the infrared detection signal.

As another example, the proximity sensor 151 may include an infrared module including an infrared light source and an infrared sensor. The infrared module may emit infrared light toward the front of the display apparatus 100 using the infrared light source, and detect infrared light reflected by a user using the infrared sensor. Further, the infrared module may transmit an infrared detection signal indicating whether or not infrared light is detected, to the controller 180. The controller 180 may determine whether the user approaches the display apparatus 100 based on the infrared detection signal.

The storage 160 may include a storage medium 161 configured to store programs and data for controlling the operation of the display apparatus 100. Further, the storage 160 may include a storage management circuit including a processor and/or memory configured to manage data stored in the storage medium 161.

For example, the storage medium 161 may store an operating system (OS) that manages resources, for example, software and/or hardware, included in the display apparatus 100, a video player configured to decode content data, and restore images, a payment management program for purchasing and payment of products, and an information protection program for preventing leakage of payment information.

In addition, the storage medium 161 may store content data displayed by the display apparatus 100. For example, the storage 160 may store an image file that is generated by compressing/encoding content data.

The storage medium 161 may include a non-volatile memory to preserve stored programs and data even when the power is cut off. For example, the storage medium 161 may include a flash memory, a solid state drive (SSD), a hard disc drive, or an optical disc drive.

The communication circuitry 170 may include a wired communication module 171 configured to receive content data from a content source in a wired manner, and a wireless communication module 172 configured to receive content data from a content source in a wireless manner.

The wired communication module 171 may receive content data from a content source through various types of video transmission cables. For example, the wired communication module 171 may receive content data from a content source through a component (YPbPr/RGB) cable or a composite video blanking and sync (CVBS) cable or a High Definition Multimedia Interface (HDMI) cable.

In addition, the wired communication module 171 may receive content data from a content source using various communication standards. For example, the wired communication module 171 may receive content data from a content source using Ethernet (IEEE 802.3 technology standard).

The wired communication module 171 may include a communication circuit including a processor and/or memory for decoding or encoding data for the wired communication.

The wireless communication module 172 may include a communication circuit configured to perform the wireless communication, and may access an access point (AP) or a communication base station (BS) using various wireless communication standards. The wireless communication module 172 may receive content data from a content source through a connection relay or a communication base station.

For example, the wireless communication module 172 may be connected to a connection relay by using a wireless communication standard such as Wi-Fi™, (IEEE 802.11 technology standard) or Bluetooth™ (IEEE 802.15.1 technology standard) or ZigBee™ (IEEE 802.15.4 technology standard), and receive content data from a content source via the connection relay. In addition, a wireless receiver module may be connected to a communication base station using a wireless communication standard such as CDMA, WCDMA, GSM, LTE, and WiBro, and receive content data from a content source through the communication base station.

The wired communication module 171 may include an antenna for transmitting and receiving wireless signals and a communication circuit including a processor and/or memory for decoding or encoding data for the wireless communication.

The controller 180 may include a processor 181 configured to process content data and a user touch input, and a memory 182 configured to memorize or store content data and processing data such as a user touch input.

The memory 182 may store programs and data for processing content data, and temporarily memorize temporary content data that is generated while processing the content data.

The memory 182 may store programs and data for controlling the display apparatus 100, and temporarily memorize temporary control data generated while controlling the display apparatus 100.

The memory 182 may include non-volatile memory such as a read only memory (ROM) and a flash memory for storing data for a long time, and volatile memory such as a static random access memory (S-RAM), and a dynamic random access memory (D-RAM) for temporarily storing data.

The processor 181 may decode content data stored in the storage 160 or content data received through the communication circuitry 170 and output image data and sound data which are decoded from the content data. The image data may be output to the display apparatus 100. The sound data may be converted into an analog sound signal through a digital-to-analog converter, and the analog sound signal may be output to the sound portion 130.

The processor 181 may output image data of an image inducing a user command or a user selection to the display 120 and receive touch data indicating a user touch position from the infrared touch frame 110. The processor 181 may identify a user command, that is, a user touch input, based on the image data and the touch data. The processor 181 may output image data for displaying an image in response to a user touch input to the display 120.

In addition, the processor 181 may control the display sterilization portion 140 based on the reception of the user touch input.

For example, when the user touch input is not detected, the processor 181 may output a sterilization control signal that allows the display sterilization portion 140 to sterilize the surface of the display panel 103. Particularly, when the infrared sensor 112 detects infrared light emitted from the infrared light source 111, that is, when all of the plurality of IR photodiodes 220 detects infrared light emitted from the plurality of IR LEDs 210, the processor 181 may output the sterilization control signal for driving the plurality of UV LEDs 230.

As another example, when a touch input indicating the end of the service, which is provided by the display apparatus 100 to the user, is received, the processor 181 may output the sterilization control signal that allows the display sterilization portion 140 to sterilize the surface of the display panel 103.

The processor 181 may include an operation circuit configured to perform logical operations and arithmetic operations, and a memory circuit configured to memorize data that is operated.

As mentioned above, when the user touch input is not detected, the controller 180 may sterilize the surface of the display panel 103. In addition, when a touch input for terminating the service is received, the controller 180 may sterilize the surface of the display panel 103.

The controller 180 may include the processor 181 and the memory 182 which are configured to process content data and touch input. The processor 181 and the memory 182 may be mounted on a control assembly 106 illustrated in FIG. 3. Further, the storage 160 and the communication circuitry 170 may also be mounted on the control assembly 106.

The control assembly 106 may include a printed circuit board and a control circuit mounted on the printed circuit board. For example, the control circuit may include a memory, a microprocessor and a metal pattern, which may be for example a control line, connecting them.

The control assembly 106 may be supported or fixed by the bottom chassis 108 as illustrated in FIG. 3.

The power supply 190 may supply power to all components of the display apparatus 100. For example, the power supply 190 may supply power to the infrared touch frame 110, the display 120, the sound portion 130, the display sterilization portion 140, the user detector 150, the storage 160, the communication circuitry 170 and the controller 180.

For example, the power supply 190 may include a power supply circuit 191 configured to receive an AC power from an external power supply and convert the received AC power into DC power, and a power control circuit 192 configured to control the power supply circuit to regulate a voltage applied to the display 120. The power supply circuit 191 may include a switching mode power supply (SMPS).

The power supply circuit 191 and the power control circuit 192 of the power supply 190 may be mounted to a power assembly 107 as illustrated in FIG. 3.

The power assembly 107 may include a printed circuit board and a power circuit mounted on the printed circuit board. For example, the power supply circuit may include a capacitor, a coil, a resistance element, a microprocessor, and a metal pattern (power supply line) connecting them.

Figure 6:
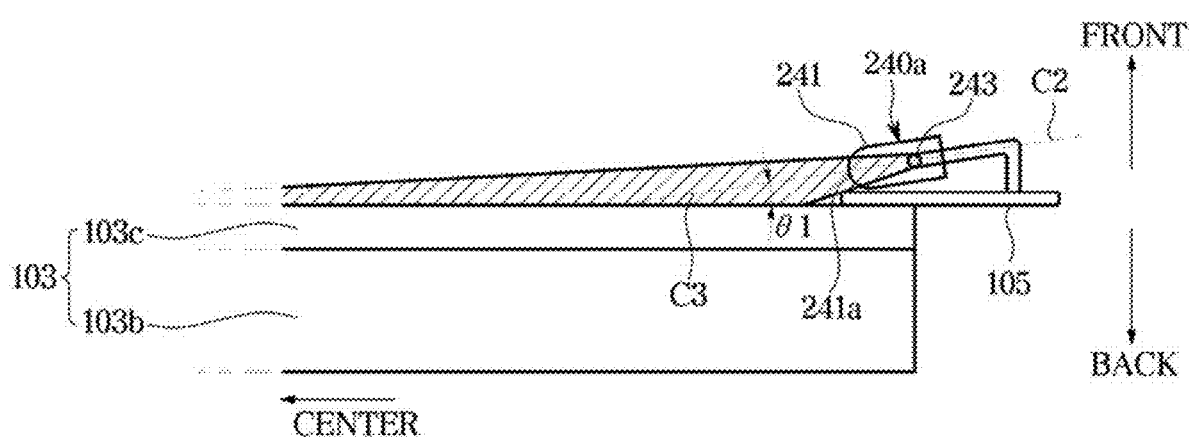
FIG. 6 is a view illustrating an example of a direction in which the UV light source included in the display apparatus according to an embodiment emits ultraviolet light, according to an embodiment.

FIG. 6 is a view illustrating an example of a direction in which the UV light source included in the display apparatus according to an embodiment emits ultraviolet light. Particularly, FIG. 6 illustrates an example of a side cross-section of the display panel 103 and the UV light source 141.

For example, the display panel 103 may include a display layer 103b configured to emit light to generate an image and a window cover 103c configured to protect the display layer 103b from the outside.

The display layer 103b may include a self-luminous display panel such as an inorganic light emitting diode (LED) panel, or an organic light emitting diode (OLED) panel, in which each of the plurality of pixels P emits light by itself or a non-self-luminous display panel such as a liquid crystal display (LCD) panel in which each of the plurality of pixels P transmits or blocks light emitted from the backlight unit.

The window cover 103c may be formed of tempered glass or transparent resin, and may protect the display layer 103b from external impact or foreign objects.

The UV light source 141 may include an UV LED 240a.

The UV LED 240a may include a LED chip 243 configured to emit ultraviolet light and a first lens 241 configured to protect the LED chip 243 and focus the ultraviolet light emitted from the LED chip 243.

The LED chip 243 may emit ultraviolet light radially with respect to a central axis C2 of the UV LED 240a. The light emitted from the UV LED 240a may be refracted while passing through the surface of the first lens 241.

As an example, the first lens 241 may be a cylindrical shape having one end with a spherical shape. Particularly, the first lens 241 may be approximately symmetrical with respect to the central axis C2 of the UV LED 240a.

Therefore, light refracted on a spherical surface 241a of the first lens 241 may be concentrated with respect to the central axis C2 of the UV LED 240a. Therefore, the central axis C2 of the UV LED 240a may approximately coincide with a main optical axis C3 having the highest intensity of ultraviolet light emitted from the UV LED 240a.

The UV LED 240a may be provided in front of the window cover 103c, for example on outside the window cover 103c, as illustrated in FIG. 6. Particularly, the UV LED 240a may be mounted on the front frame 105. The front frame 105 may be provided in front of the edge portion of the window cover 103c. The UV LED 240a may also be provided in front of the edge portion of the window cover 103c.

The UV LED 240a may be disposed in such a way that the spherical surface 241a of one end of the UV LED 240a faces the center of the window cover 103c. Therefore, the UV LED 240a may emit ultraviolet light from the edge portion of the window cover 103c toward the center of the window cover 103c, for example in a center direction as illustrated in FIG. 6.

In addition, the UV LED 240a may be disposed to be inclined toward the window cover 103c. In other words, the UV LED 240a may be disposed in such a way that the spherical surface 241a of one end of the UV LED 240a faces the window cover 103c. Therefore, the UV LED 240a may emit ultraviolet light obliquely toward the window cover 103c from the outside of the window cover 103c.

For example, as illustrated in FIG. 6, the main optical axis C3 of ultraviolet light may not be in parallel with the surface of the window cover 103c. An included angle Θ1 between the main optical axis C3 of the ultraviolet light and the surface of the window cover 103c may be an acute angle less than 90 degrees.

Therefore, the main optical axis C3 having the highest intensity of ultraviolet light emitted from the UV LED 240a may not be in parallel with the surface of the window cover 103c. In addition, the included angle Θ1 between the main optical axis C3 of ultraviolet light and the surface of the window cover 103c may be an acute angle less than 90 degrees.

With respect to a direction in which the UV LED 240a is in parallel with the window cover 103c, an angle Θ1 inclined toward the window cover 103c may depend on a width of the display panel 103 and the intensity of the ultraviolet light emitted from the UV LED 240a.

As mentioned above, the UV LED 240a may emit ultraviolet light obliquely toward the surface of the window cover 103c in such a way that the included angle between the main optical axis C3 of the ultraviolet light and the surface of the window cover 103c is acute. Accordingly, the UV LED 240a may emit ultraviolet light, which is spread around the main optical axis C3 and has the high intensity, to the surface of the window cover 103c and thus it is possible to improve the sterilization effect.

Figure 7:
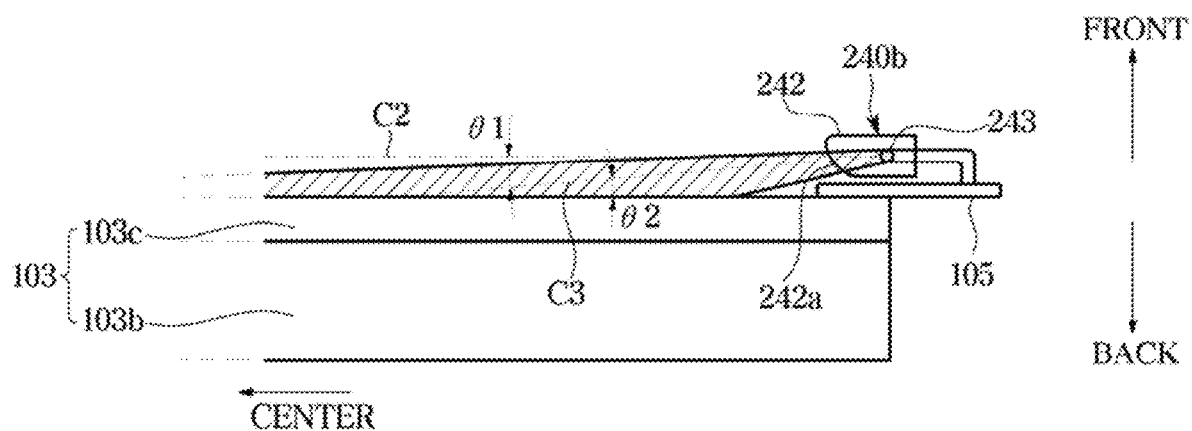
FIG. 7 is a view illustrating another example of the direction in which the UV source included in the display apparatus according to an embodiment emits ultraviolet light, according to an embodiment.

FIG. 7 is a view illustrating another example of the direction in which the UV source included in the display apparatus according to an embodiment emits ultraviolet light. Particularly, FIG. 7 illustrates another example of a side cross-section of the display panel 103 and the UV light source 141.

As illustrated in FIG. 6, the display panel 103 may include the display layer 103b and the window cover 103c.

In addition, the UV light source 141 may include an UV LED 240b. The UV LED 240b may include a LED chip 243 and a second lens 242.

The second lens 242 may have an obliquely truncated cylinder shape. Particularly, the second lens 242 may include a round bevel 242a formed at an angle to the cylinder. Therefore, ultraviolet light emitted from the LED chip 243 may be deflected and concentrated from a central axis C2 of the UV LED 240b. In other words, a main optical axis C3 having the highest intensity of ultraviolet light emitted from the UV LED 240b may be different from a center axis C2 of the UV LED 240b. An included angle Θ2 between the main optical axis C3 of ultraviolet light and the central axis C2 of the UV LED 240b may be an acute angle less than 90 degrees.

The UV LED 240b may be provided in front of the window cover 103c, for example on the outside of the window cover 103c, as illustrated in FIG. 7.

The UV LED 240b may be disposed in such a way that the round bevel 242a of one end of the UV LED 240b faces the center of the window cover 103c. Therefore, the UV LED 240b may emit ultraviolet light from the edge portion of the window cover 103c toward the center of the window cover 103c, for example in the center direction as illustrated in FIG. 7.

In addition, the UV LED 240b may be disposed in such a way the central axis C2 thereof is substantially in parallel with the window cover 103c. The round bevel 242a of the second lens 242 may face the window cover 103c of the display panel 103. The ultraviolet light emitted from the LED chip 243 may be refracted toward the window cover 103c from the round bevel 242a of the second lens 242. Therefore, the main optical axis C3 of the ultraviolet light emitted from the UV LED 240b may be inclined toward the window cover 103c. Therefore, the UV LED 240b may emit ultraviolet light obliquely toward the window cover 103c from the outside of the window cover 103c.

For example, as illustrated in FIG. 7, the main optical axis C3 of ultraviolet light may not be in parallel with the surface of the window cover 103c. An included angle Θ2 between the main optical axis C3 of ultraviolet light and the surface of the window cover 103c may be an acute angle less than 90 degrees.

The angle at which the round bevel 242a of the UV LED 240b is inclined may depend on the width of the display panel 103 and the intensity of ultraviolet light emitted from the UV LED 240b. In other words, the included angle Θ2 between the main optical axis C3 of the ultraviolet light and the surface of the window cover 103c may depend on the width of the display panel 103 and the intensity of ultraviolet light emitted from the UV LED 240b.

Figure 8A:
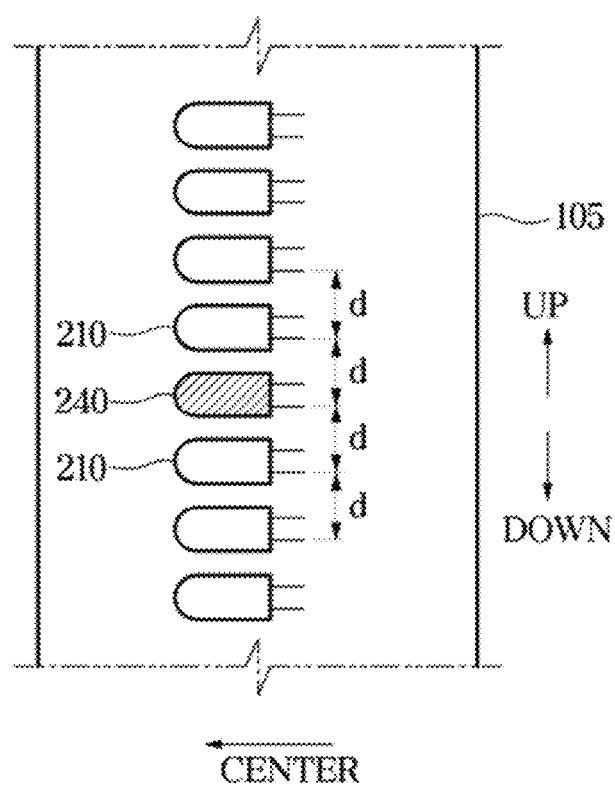
FIGS. 8A, 8B and 8C are views illustrating an example of placing the UV light source included in the display apparatus according to an embodiment.
Figure 8B:
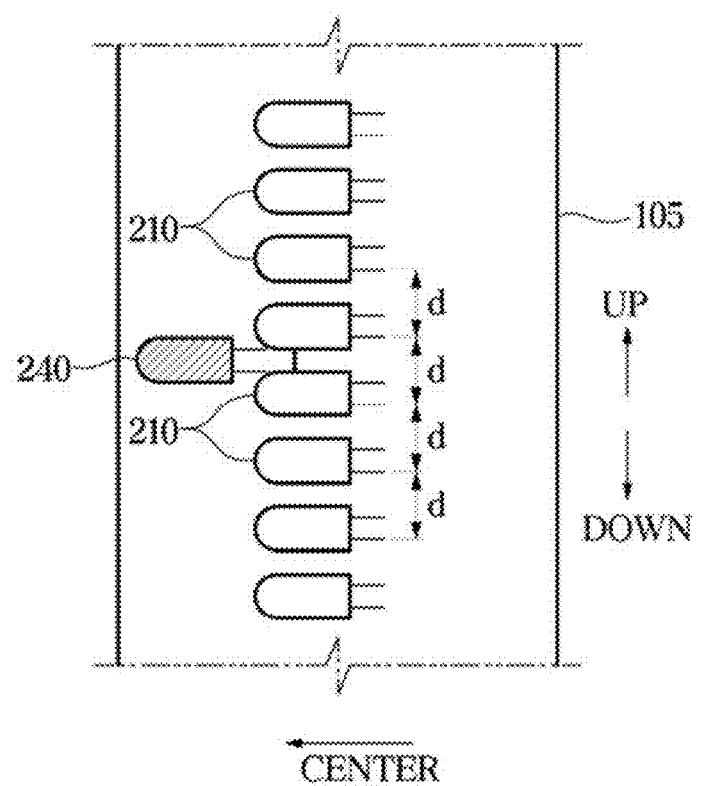
Figure 8C:
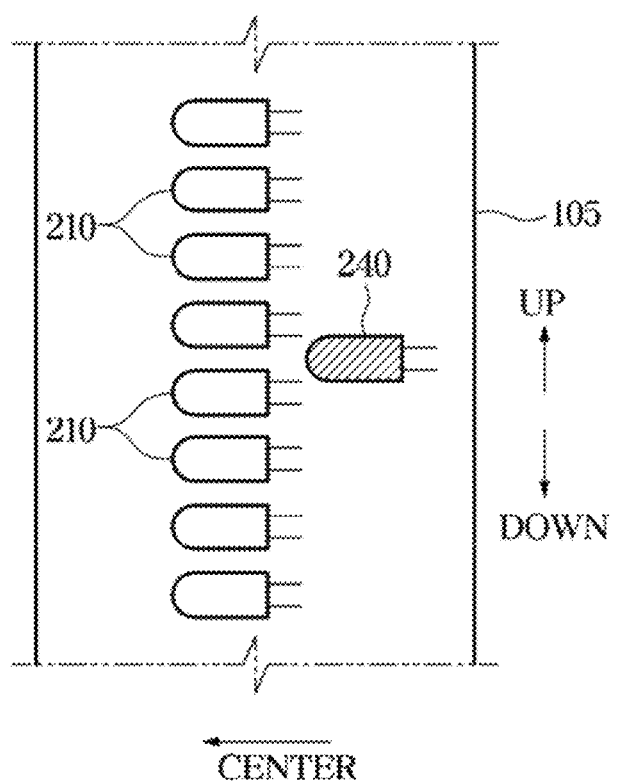

FIGS. 8A, 8B and 8C are views illustrating an example of placing the UV light source included in the display apparatus according to an embodiment.

An ultraviolet light emitting diode (UV LED) 240 may be installed on the front frame 105 together with a plurality of IR LEDs 210, or the plurality of IR photodiodes. For example, the UV LED 240 may be installed on the front frame 105 at the same height as the plurality of IR LEDs 210. In other words, the UV LED 240 and the plurality of IR LEDs 210 may be located on the same plane on the front frame 105.

The UV LED 240 and the plurality of IR LEDs 210 may be installed in such a way that ultraviolet light of the UV LED 240 do not interfere with the plurality of IR LEDS 210 or the infrared light of the plurality of IR LEDs 210 do not interfere with the UV LED 240.

As illustrated in FIG. 8A, the UV LED 240 may replace any one of the plurality of IR LEDs 210, or the plurality of IR photodiodes. In other words, a distance d between the UV LED 240 and the adjacent IR LED 210 may be the same as a distance d among the plurality of IR LEDs 210.

Due to the arrangement as illustrated in FIG. 8A, the ultraviolet light of the UV LED 240 may not interfere with the plurality of IR LEDs 210, and the infrared light of the plurality of IR LEDs 210 may not interfere with the UV LED 240. Further, it may be possible to minimize a thickness of the front bezel 102a in which the UV LED 240 and the plurality of IR LEDs 210 are placed.

As illustrated in FIGS. 8B and 8C, the UV LED 240 may be disposed in a line different from a line in which the plurality of IR LEDs 210, or the plurality of IR photodiodes, is arranged. In comparison with the plurality of IR LEDs 210, or the plurality of IR photodiodes, the UV LED 240 may be positioned closer to the center of the display panel 103, as illustrated in FIG. 8B, or the UV LED 240 may be positioned further from the center of the display panel 103 as illustrated in FIG. 8C.

Due to the arrangement illustrated in FIGS. 8B and 8C, the plurality of IR LEDs 210 may be disposed at regular distances, and the infrared touch frame 110 may receive a user touch input with uniform resolution. In addition, it is possible to minimize a thickness of the front bezel 102a in which the UV LED 240 and the plurality of IR LEDs 210 are placed.

Figure 9A:
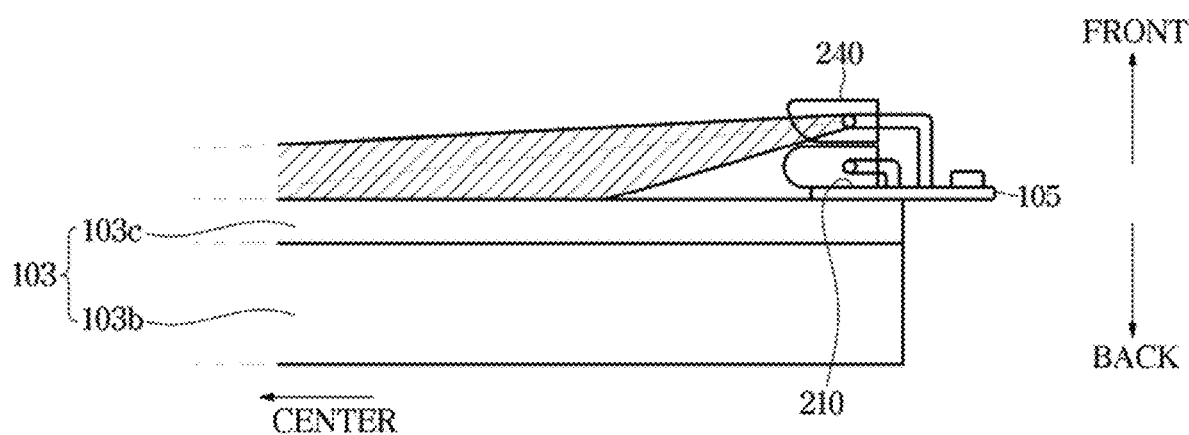
FIGS. 9A and 9B are views illustrating another example of placing the UV light source included in the display apparatus according to an embodiment.
Figure 9B:
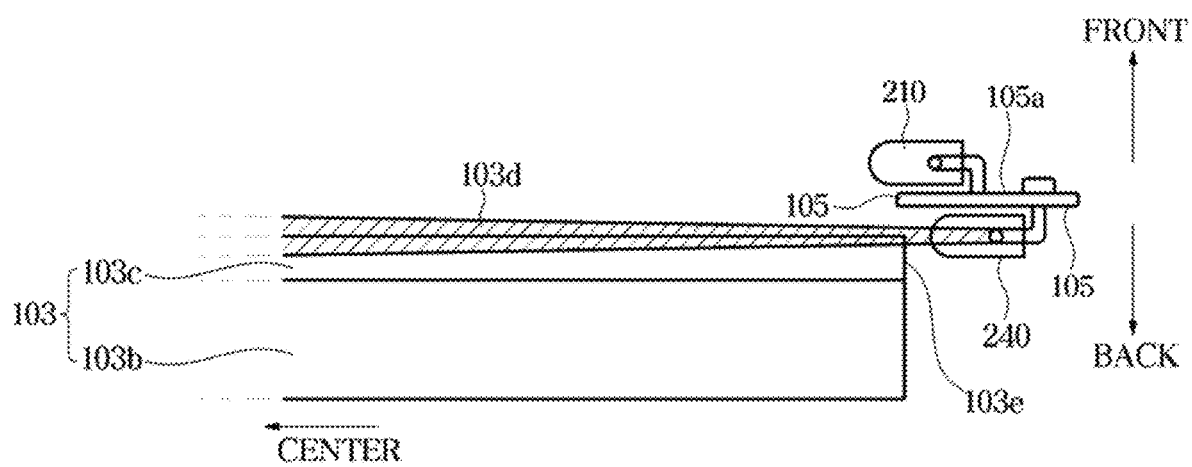

FIGS. 9A and 9B are views illustrating another example of placing the UV light source included in the display apparatus according to an embodiment.

The UV LED 240 may be installed on the front frame 105 together with the plurality of IR LEDs 210, or the plurality of IR photodiodes. For example, the UV LED 240 may be installed on the front frame 105 at a different height from the plurality of IR LEDs 210. In other words, the UV LED 240 may be located on a different plane from the plurality of IR LEDs 210.

As illustrated in FIG. 9A, the UV LED 240 may be installed in front of the plurality of IR LEDs 210, or the plurality of IR photodiodes. For example, the plurality of IR LEDs 210 may be installed on the front frame 105, and the UV LED 240 may be installed on the plurality of IR LEDs 210.

Due to the arrangement as illustrated in FIG. 9A, the ultraviolet light of the UV LED 240 may not interfere with the plurality of IR LEDs 210, and the infrared light of the plurality of IR LEDs 210 may not interfere with the UV LED 240. Further, the plurality of IR LEDs 210 may be disposed at regular distances, and thus the infrared touch frame 110 may receive a user touch input with uniform resolution.

As illustrated in FIG. 9B, the UV LED 240 may be installed behind the plurality of IR LEDs 210, or the plurality of IR photodiodes. For example, the plurality of IR LEDs 210 may be installed on a first surface 150a of the front frame 105, and the UV LED 240 may be installed on a second surface 150b of the front frame 105.

In embodiments, at least a portion of the UV LED 240 may overlap the window cover 103c of the display panel 103. In other words, the UV LED 240 may emit ultraviolet light toward a front surface 103d of the window cover 103c and a side surface 103e of the window cover 103c.

Some of the ultraviolet rays emitted from the UV LED 240 may be emitted toward the front surface 103d of the window cover 103c. The ultraviolet rays emitted toward the front surface 103d of the window cover 103c may sterilize the front surface 103d of the window cover 103c.

In addition, another of the ultraviolet rays emitted from the UV LED 240 may be projected into the window cover 103*c* through the side surface 103*e* of the window cover 103*c*. The ultraviolet rays may be emitted through the front surface 103*d* of the window cover 103*c* by refraction, reflection, or total reflection, or scattering while passing through the inside of the window cover 103*c*. The ultraviolet rays emitted through the front surface 103*d* of the window cover 103*c* may sterilize the front surface 103*d* of the window cover 103*c*.

Due to the arrangement as illustrated in FIG. 9B, the ultraviolet light of the UV LED 240 may not interfere with the plurality of IR LEDs 210, and the infrared light of the plurality of IR LEDs 210 may not interfere with the UV LED 240. Further, the plurality of IR LEDs 210 may be disposed at regular distances, and thus the infrared touch frame 110 may receive a user touch input with uniform resolution.

In addition, it is possible to minimize a thickness of the front bezel 102*a* in which the UV LED 240 and the plurality of IR LEDs 210 are placed.

As mentioned above, the UV LED 240 configured to sterilize the surface of the display panel 103 may be disposed among the plurality of IR LEDs 210 in a variety of ways.

Figure 10:
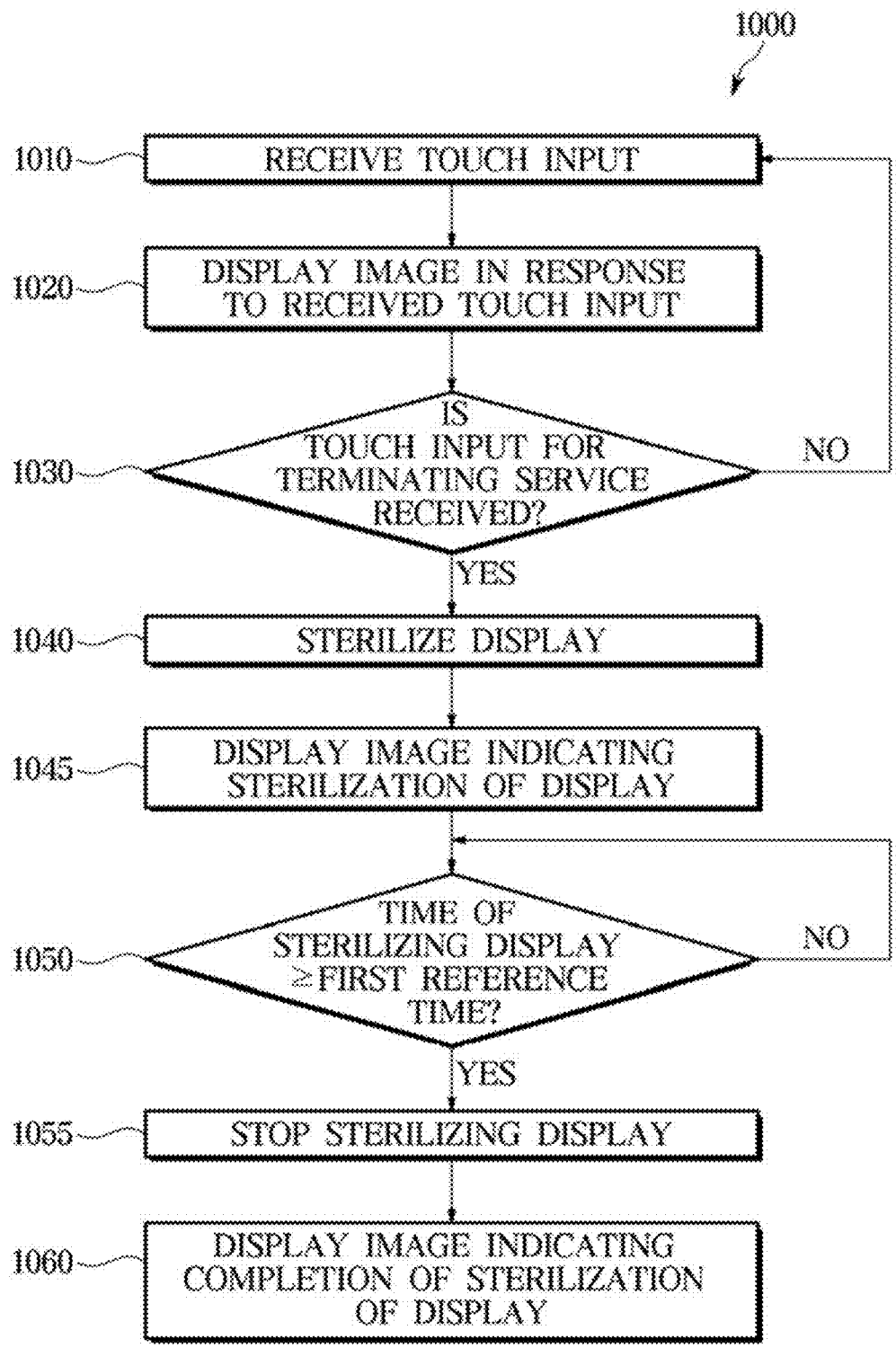
FIG. 10 is a flowchart illustrating an example of a sterilization operation of the display apparatus according to an embodiment.
Figure 11:
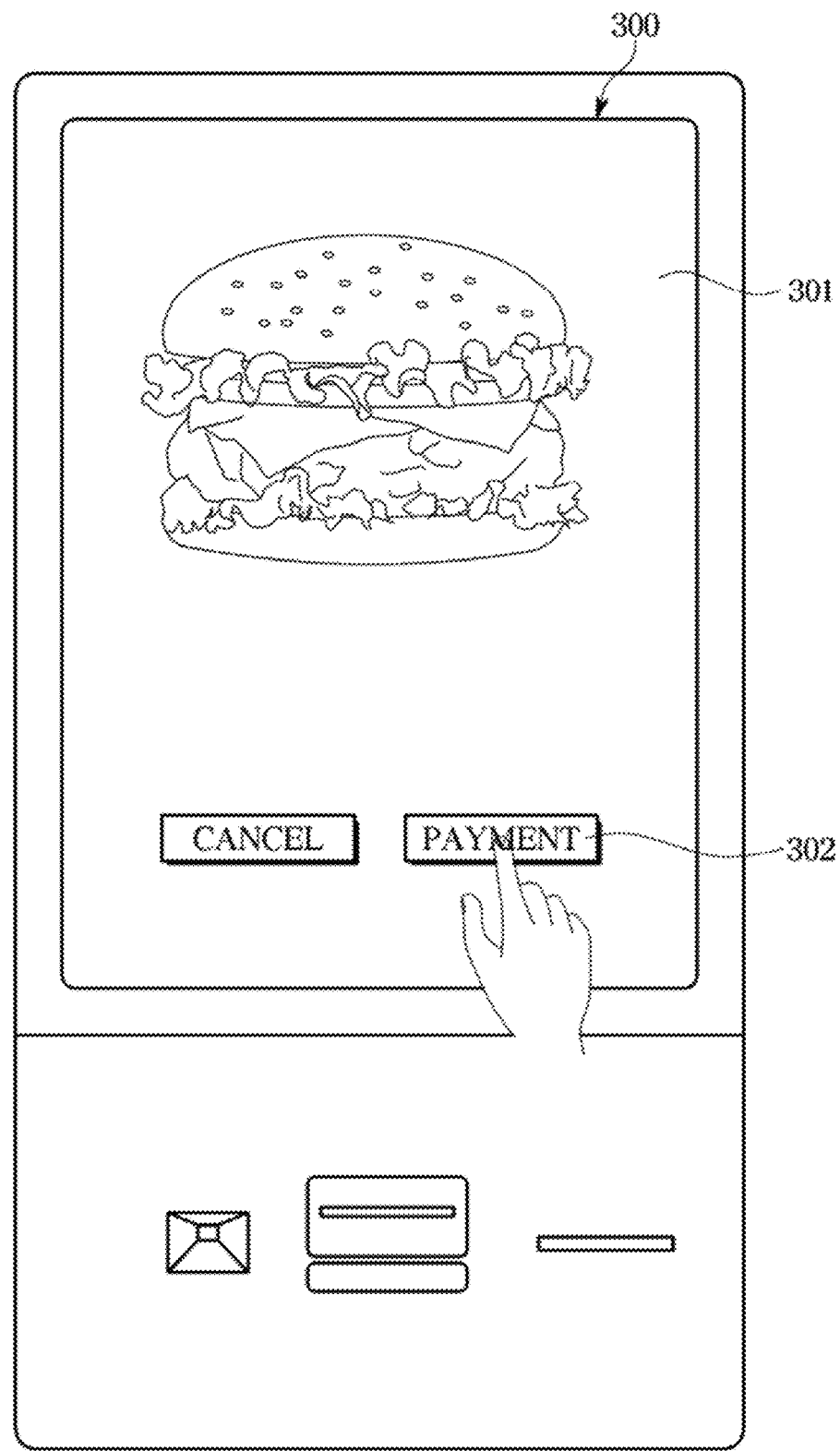
FIG. 11 is a view illustrating an example of an image for terminating a service during the sterilization operation of FIG. 10, according to an embodiment.
Figure 12:
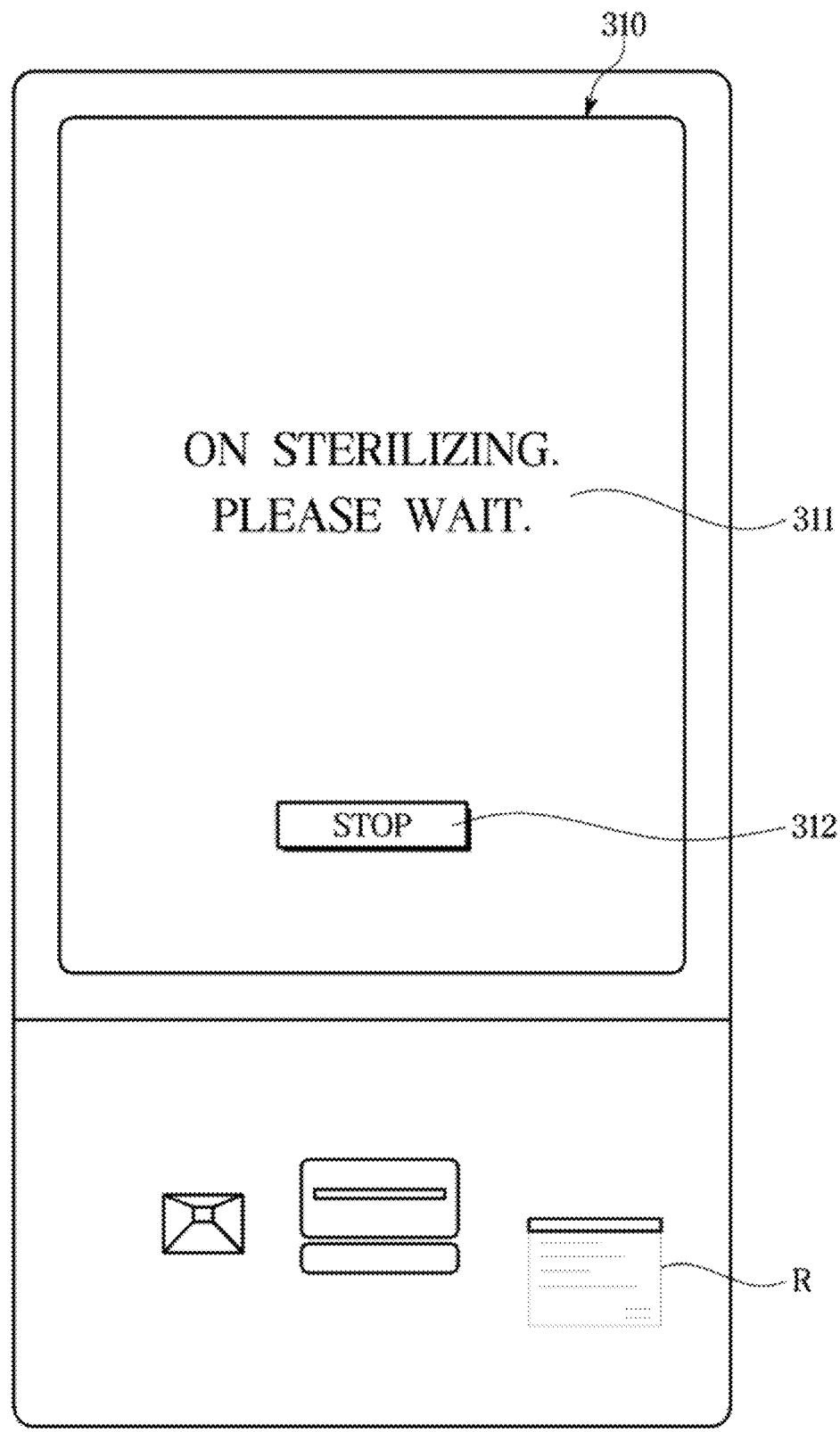
FIG. 12 is a view illustrating an example of an image indicating sterilization of a display during the sterilization operation of FIG. 10, according to an embodiment.
Figure 13:
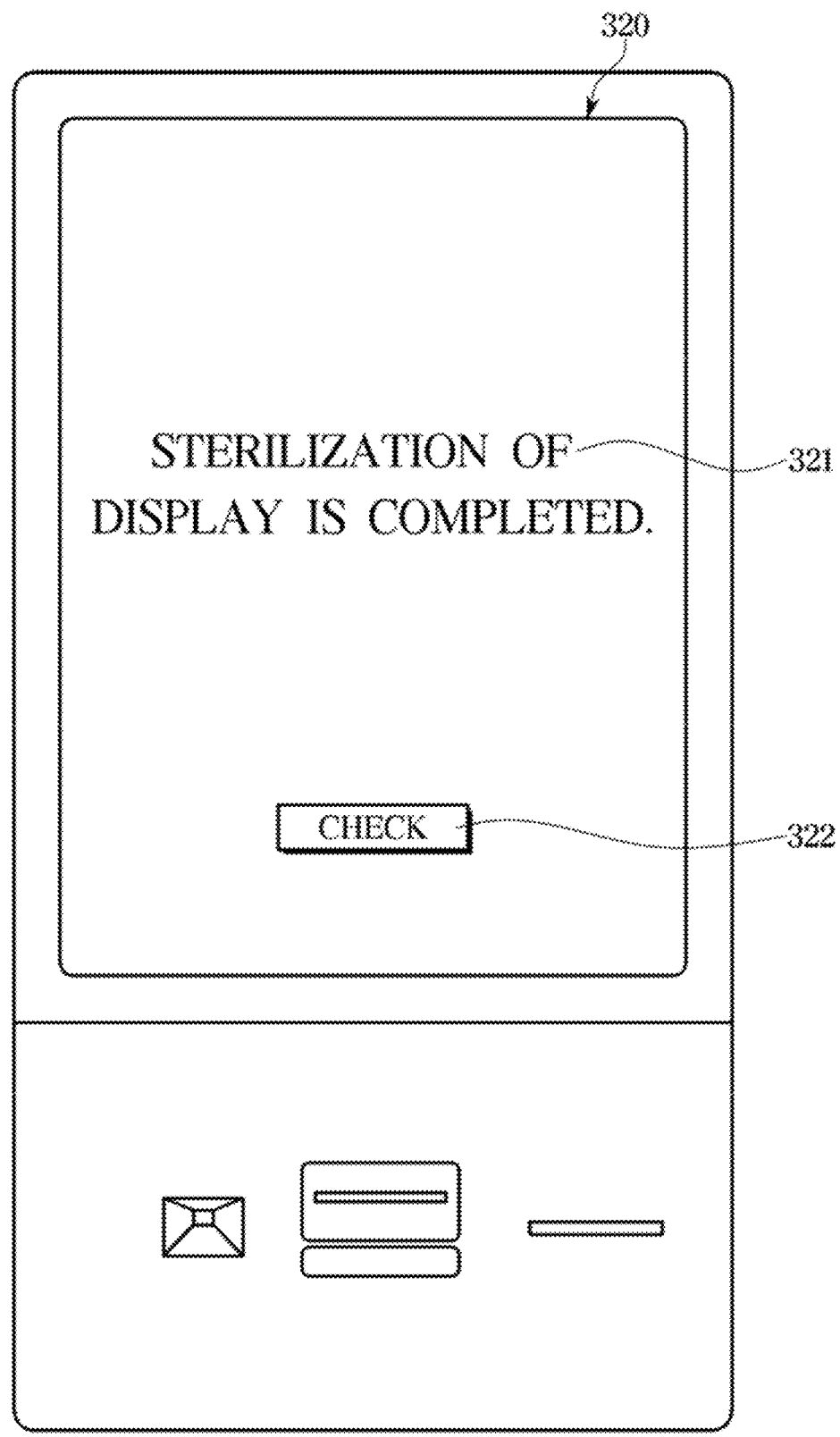
FIG. 13 is a view illustrating an example of an image indicating completion of sterilization of the display during the sterilization operation of FIG. 10, according to an embodiment.

FIG. 10 is a flowchart illustrating an example of a sterilization operation of the display apparatus according to an embodiment. FIG. 11 is a view illustrating an example of an image for terminating a service during the sterilization operation of FIG. 10. FIG. 12 is a view illustrating an example of an image indicating sterilization of a display during the sterilization operation of FIG. 10. FIG. 13 is a view illustrating an example of an image indicating completion of sterilization of the display during the sterilization operation of FIG. 10.

A display sterilization operation 1000 of the display apparatus 100 will be described with reference to FIGS. 10 to 13.

The display apparatus 100 may receive a touch input from a user at operation 1010).

The controller 180 may display an image for providing a service. For example, when the display apparatus 100 is a kiosk for purchasing a product, the controller 180 may display information on products that the user can purchase on the display 120.

In addition, the controller 180 may display an image inducing a user command or a user selection on the display 120. The user may check the image displayed on the display 120 and touch the display 120 to input a command or selection.

The infrared touch frame 110 may detect a user touch and identify a touch position. Each of the plurality of IR LEDs 210 may emit infrared light, and each of the plurality of IR photodiodes 220 may detect infrared light. Some of infrared rays emitted from the plurality of IR LEDs 210 may be blocked by the user touch, and some of the plurality of IR photodiodes 220 may not detect infrared light. The infrared touch frame 110 may identify a touch position based on whether or not the plurality of IR photodiodes 220 receives infrared light.

The controller 180 may receive the user touch position from the infrared touch frame 110, and identify or determine the user command or user selection, which may be referred to as "touch input", based on the image inducing the user command or user selection and the user touch position on the display.

The display apparatus 100 may display an image in response to the user touch input at operation 1020).

The controller 180 may display an image, which is in response to the touch input obtained through the infrared touch frame 110, on the display 120. The image in response to the touch input may include an image inducing a new command or a new selection. Further, the image in response to the touch input may include information on a product selected by the user, for example, shape, size, price and quantity.

The display apparatus 100 may determine whether or not a touch input for terminating the service is received at operation 1030.

The controller 180 may identify whether or not the user touch input is a touch input indicating termination of a service for the user, based on the image of the display 120 and the user touch input.

For example, when the display apparatus 100 is a kiosk for purchase of a product, the controller 180 may display a payment screen 300, which is to receive a touch input for a user to pay for the product, on the display 120 as illustrated in FIG. 11.

The payment screen 300 may include information 301 of the product selected by the user, for example, shape, price, and quantity. In addition, the payment screen 300 may include a payment button 302 for a user to select a payment for a product price. When the user touches the payment button 302 of the payment screen 300, payment of the product may be performed. In addition, when the payment button 302 of the payment screen 300 is touched, the controller 180 may determine that a touch input for terminating the service for the corresponding user is input.

As another example, when the display apparatus 100 is an automated teller machine (ATM), the controller 180 may display a screen including a withdrawal button for withdrawing cash on the display 120. When the user touches the withdrawal button, the display apparatus 100 may discharge cash. In addition, when the withdrawal button is touched, the controller 180 may determine that a touch input for terminating the service for the corresponding user is input.

As another example, when the display apparatus 100 is a portable terminal device, the controller 180 may display a screen including an end button for turning off the portable terminal device on the display 120. When the user touches the end button, the display apparatus 100 may turn off the power. In addition, when the end button is touched, the controller 180 may determine that a touch input for terminating the service for the corresponding user is input.

When it is determined that a touch input for terminating the service is not received (no at operation 1030), the display apparatus 100 may receive a user touch input and display an image in response to the user touch input.

When it is determined that a touch input for terminating the service is received (yes at operation 1030), the display apparatus 100 may sterilize the display 120, or begin sterilizing the display 120, at operation 1040.

Upon receiving the touch input for terminating the service, the controller 180 may determine that the user will not additionally input the touch input. In other words, because the display apparatus 100 provides all services to the user, the display apparatus 100 may determine that the user will not input an additional command.

Therefore, the controller 180 may sterilize the display 120, which may be contaminated by the user touch, without the user being exposed to ultraviolet light.

In order to sterilize the surface of the display panel 103, the controller 180 may drive the UV light source 141 included in the display sterilization portion 140. For example, the controller 180 may drive the plurality of UV LEDs 230 installed on the front frame 105 to emit ultraviolet light toward the surface of the display panel 103.

The plurality of UV LEDs 230 may emit ultraviolet light toward the surface of the display panel 103, and thus the surface of the display panel 103 may be sterilized by the ultraviolet light.

Upon receiving a touch input for terminating the service, the display apparatus 100 may perform an operation for terminating the service. The controller 180 may sterilize the surface of the display panel 103 together with an operation for terminating the service. For example, when payment for a product is made, the kiosk may issue a receipt R. The controller 180 may allow the plurality of UV LEDs 230 to sterilize the surface of the display panel 103 while the kiosk issues the receipt R, as illustrated in FIG. 12.

During the sterilization of the display 120, the display apparatus 100 may display an image indicating the sterilization of the display 120 at operation 1045.

During the sterilization of the display 120, that is, during the drive of the plurality of UV LEDs 230, the controller 180 may display a sterilization progress screen 310 indicating sterilization of the display 120, on the display 120.

For example, the sterilization progress screen 310 may include a guide message 311 indicating that the display 120 is being sterilized, as illustrated in FIG. 12. The sterilization progress screen 310 may also include a stop button 312 to stop the sterilization of the display 120. When the touch of the stop button 312 is detected, the controller 180 may stop the sterilization of the display 120. In other words, the controller 180 may stop driving of the plurality of UV LEDs 230.

During the sterilization of the display 120, the display apparatus 100 may determine whether or not a time of sterilizing the display 120 is equal to or greater than a first reference time at operation 1050.

During the sterilization of the display 120, for example during the drive of the UV light source 141, the controller 180 may count a time of driving the UV light source 141. In addition, the controller 180 may compare the driving time of the UV light source 141 with the first reference time.

The first reference time may be set experimentally or empirically. For example, the first reference time may be set based on a period of time until a next user uses the display apparatus 100 from when the service of the display apparatus 100 for the user ends. As another example, the first reference time may be set based on a period of time in which bacteria on the surface of the display 120 are sterilized by 99% or more by ultraviolet light emitted from the plurality of UV LEDs 230.

When the time of sterilizing the display 120 is less than the first reference time (no at operation 1050), the display apparatus 100 may continue to sterilize the display 120. In other words, the controller 180 may continue to drive the plurality of UV LEDs 230.

When the time of sterilizing the display 120 is equal to or greater than the first reference time (yes at operation 1050), the display apparatus 100 may stop the sterilization of the display 120 at operation 1055.

When the time of sterilizing the display 120 is equal to or greater than the first reference time, the controller 180 may terminate the sterilization of the display 120 to allow another user to use the display apparatus 100. For example, the controller 180 may stop driving of the plurality of UV LEDs 230.

The display apparatus 100 may display an image indicating completion of sterilization of the display 120 at operation 1060.

At the same time as terminating the sterilization of the display 120 or after terminating the sterilization of the display 120, the controller 180 may display a sterilization completion screen 320 indicating the sterilization completion of the display 120 on the display 120.

For example, the sterilization completion screen 320 may include a guide message 321 indicating that the sterilization of the display 120 is completed, as illustrated in FIG. 13. The sterilization completion screen 320 may also include a confirmation button 322 configure to receive a new user input after the sterilization of the display 120. When the touch of the confirmation button 322 is detected, or when a predetermined time is expired after the sterilization completion, the controller 180 may display a screen for receiving a new user input.

As mentioned above, the display apparatus 100 may sterilize the display 120 in response to the touch input for the termination of the service provided to the user. Accordingly, the display apparatus 100 may sterilize the display 120, which may be contaminated by the user touch, without the user being exposed to Ultraviolet light.

Figure 14:
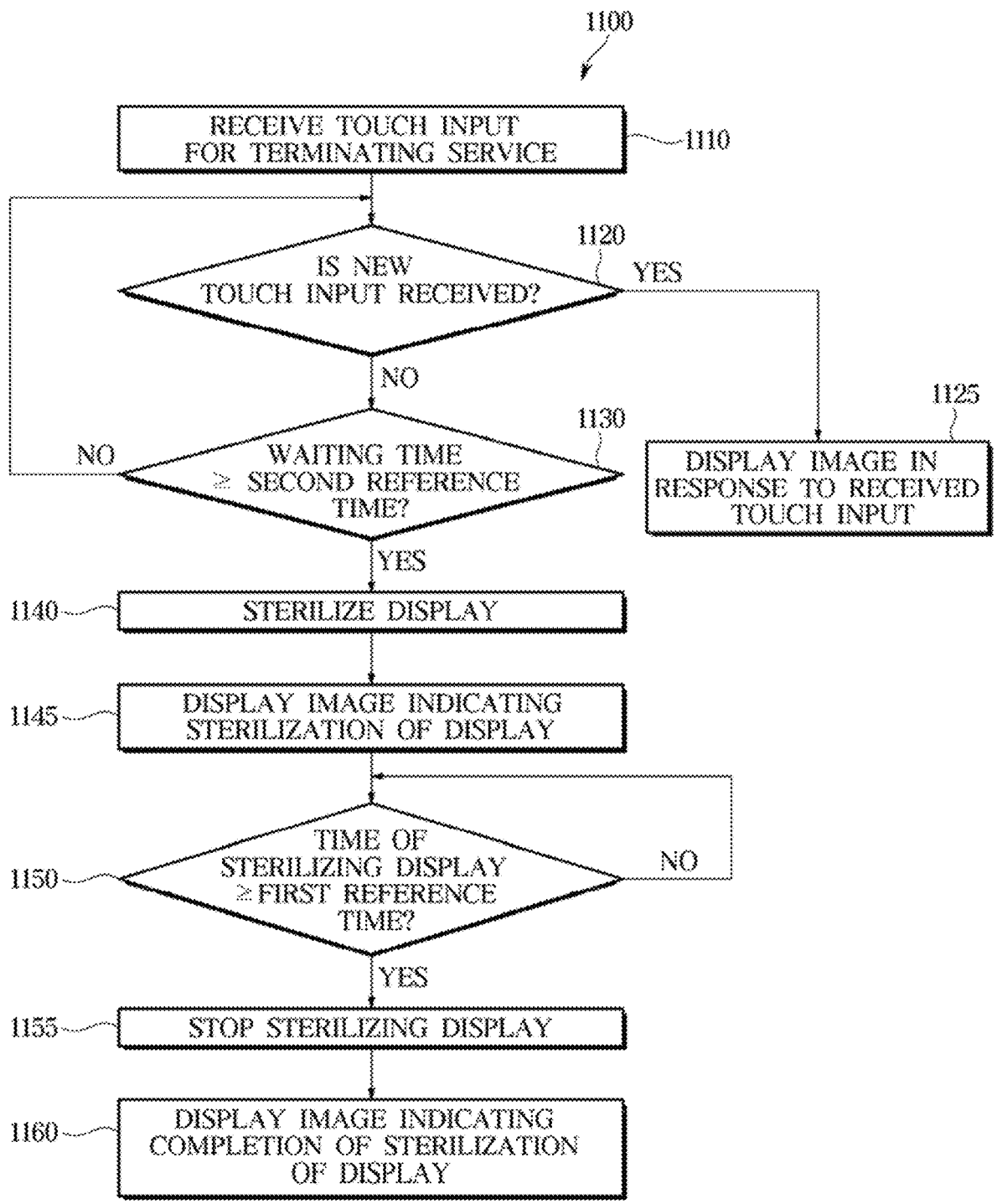
FIG. 14 is a flowchart illustrating another example of the sterilization operation of the display apparatus according to an embodiment.

FIG. 14 is a flowchart illustrating another example of the sterilization operation of the display apparatus according to an embodiment.

A display sterilization operation 1100 of the display apparatus 100 will be described with reference to FIG. 14.

The display apparatus 100 may receive a touch input for terminating the service at operation 1110.

The controller 180 may display an image for providing a service. For example, the controller 180 may display an image inducing the user command or the user selection on the display 120. In addition, the controller 180 may receive a user touch input in response to an image of the display 120.

The controller 180 may receive a touch input for terminating the service provided to the user. For example, the controller 180 may display a screen, for example, a payment screen for a product price, for terminating the service provided to the user, and may receive a touch input in response to the screen.

After receiving the touch input for terminating the service, the display apparatus 100 may determine whether a new touch input is received at operation 1120.

The display apparatus 100 may still activate the infrared touch frame 110 and receive the user touch input even after receiving the touch input for terminating the service. Further, the controller 180 may determine whether or not a new touch input is received. For example, an existing user may touch the display 120 of the display apparatus 100 to receive a new service or a new user may touch the display 120 of the display apparatus 100 to receive a new service.

When a new touch input is received (yes at operation 1120), the display apparatus 100 may display an image in response to the received touch input at operation 1125.

The controller 180 may display an image, which is in response to the touch input obtained through the infrared touch frame 110, on the display 120. In other words, the controller 180 may provide a new service in response to the user touch input.

When a new touch input is not received (no at operation 1120), the display apparatus 100 may determine whether a waiting time for waiting for the touch input is equal to or greater than a second reference time at operation 1130.

The controller 180 may count a period of time that elapses after receiving the touch input for terminating the service, which is a waiting time for waiting for a new touch input. The controller 180 may compare the waiting time with the second reference time.

The second reference time may be set experimentally or empirically. For example, the second reference time may be set based on a period of time until a next user uses the display apparatus 100 from when the service of the display apparatus 100 for the user is terminated.

When the waiting time is less than the second reference time (no at operation 1130), the display apparatus 100 may determine whether a new touch input is received, and determine again whether the waiting time is equal to or greater than the second reference time.

When the waiting time is equal to or greater than the second reference time (yes at operation 1130), the display apparatus 100 may sterilize the display 120, or begin sterilizing the display 120, at operation 1140.

When the waiting time, which elapses without receiving a new touch input after receiving the touch input for terminating the service, is equal to or greater than the second reference time, the display apparatus 100 may determine that there is no other user waiting to use the display apparatus 100. In other words, when the display apparatus 100 waits for a new touch input longer than an average time for the existing user to be replaced by a new user after the existing user has finished using the display apparatus 100, the display apparatus 100 may determine that there is no other user who intends to use the display apparatus 100.

Accordingly, the controller 180 may determine that the user will not use the display apparatus 100 for a while. In other words, the controller 180 may determine that the user will not input the touch input for a while.

Therefore, the controller 180 may sterilize the display 120, which may be contaminated by the user touch, without the user being exposed to ultraviolet light.

In order to sterilize the surface of the display panel 103, the controller 180 may drive the plurality of UV LEDs 230 installed on the front frame 105 to emit ultraviolet light toward the surface of the display panel 103.

During the sterilization of the display 120, the display apparatus 100 may display an image indicating the sterilization of the display 120 at operation 1145. During the sterilization of the display 120, the display apparatus 100 may determine whether the time of sterilizing the display 120 is equal to or greater than the first reference time at operation 1150. When the time of sterilizing the display 120 is equal to or greater than the first reference time (yes at operation 1150), the display apparatus 100 may stop the sterilization of the display 120 at operation 1155. The display apparatus 100 may display an image indicating completion of sterilization of the display 120 at operation 1160.

Operations 1145, 1150, 1155 and 1160 may correspond to operations 1045, 1050, 1055 and 1060 described with reference to FIG. 10.

As mentioned above, the display apparatus 100 may determine whether or not the user uses the display apparatus 100 based on whether or not the touch input is received. During the time in which the user does not use the display apparatus 100, the display apparatus 100 may sterilize the display 120. Accordingly, the display apparatus 100 may sterilize the display 120, which may be contaminated by the user touch, without the user being exposed to Ultraviolet light.

Figure 15:
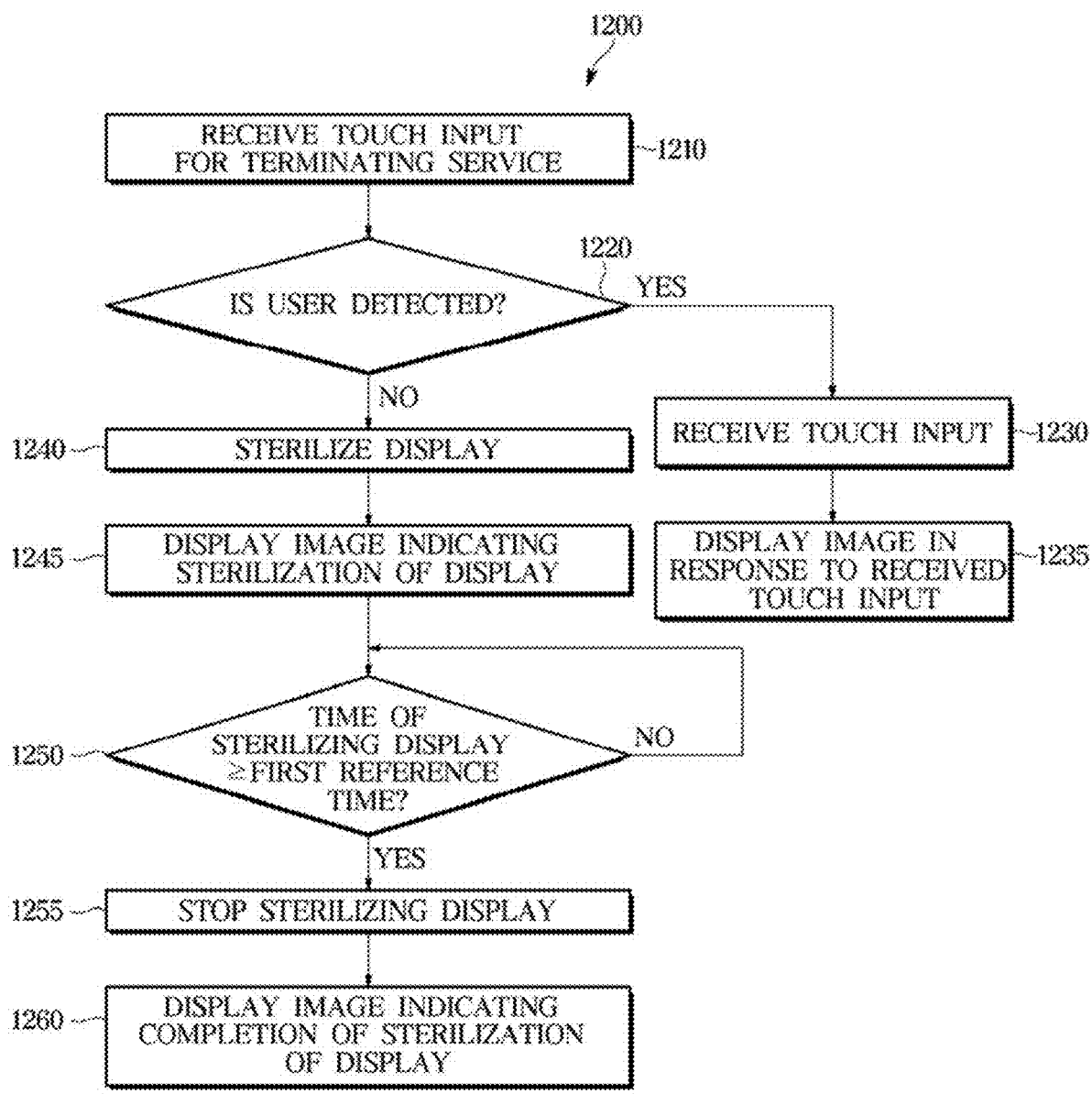
FIG. 15 is a flowchart illustrating another example of the sterilization operation of the display apparatus according to an embodiment.

FIG. 15 is a flowchart illustrating another example of the sterilization operation of the display apparatus according to an embodiment.

A display sterilization operation 1200 of the display apparatus 100 will be described with reference to FIG. 15.

The display apparatus 100 may receive a touch input for terminating the service at operation 1210.

The controller 180 may display an image for providing a service and receive a touch input for terminating the service. Operation 1210 may correspond to operation 1110 described with reference to FIG. 14.

After receiving the touch input for terminating the service, the display apparatus 100 may determine whether a user is located in front of the display 120 at operation 1220.

The display apparatus 100 may detect a user located in front of the display 120 by using the user detector 150.

For example, the user detector 150 may detect a user located in front of the display 120 based on whether or not infrared light emitted from the user is detected. When infrared light is detected, the display apparatus 100 may determine that the user is located in front of the display 120.

As another example, the user detector 150 may detect a user located in front of the display 120 based on whether or not infrared light, which is emitted to the front side of the display 120 and then reflected by the user, is detected. When infrared light reflected by the user is detected, the display apparatus 100 may determine that the user is located in front of the display 120.

When the user located in front of the display 120 is detected (yes at operation 1220), the display apparatus 100 may receive a user touch input at operation 1230. In addition, the display apparatus 100 may display an image in response to the received touch input at operation 1235.

The controller 180 may receive a user touch input through the infrared touch frame 110 and display an image in response to the received touch input on the display 120. In other words, the controller 180 may provide a new service in response to the user touch input.

When the user in front of the display 120 is not detected (no at operation 1220), the display apparatus 100 may sterilize the display 120, or begin sterilizing the display 120, at operation 1240.

When the user in front of the display 120 is not detected after receiving the touch input for terminating the service, it may be determined that there is no other user waiting to use the display apparatus 100. In other words, it may be determined that the existing user has already moved away from the display apparatus 100 and there is no other user who intends to use the display apparatus 100.

Accordingly, the controller 180 may determine that the user will not use the display apparatus 100 for a while. In other words, the controller 180 may determine that the user will not input the touch input for a while.

Therefore, the controller 180 may sterilize the display 120, which may be contaminated by the user touch, without the user being exposed to ultraviolet light.

In order to sterilize the surface of the display panel 103, the controller 180 may drive the plurality of UV LEDs 230 installed on the front frame 105 to emit ultraviolet light toward the surface of the display panel 103.

During the sterilization of the display 120, the display apparatus 100 may display an image indicating the sterilization of the display 120 at operation 1245. During the sterilization of the display 120, the display apparatus 100 may determine whether the time of sterilizing the display 120 is equal to or greater than the first reference time at operation 1250. When the time of sterilizing the display 120 is equal to or greater than the first reference time (yes at operation 1250), the display apparatus 100 may stop the sterilization of the display 120 at operation 1255. The display apparatus 100 may display an image indicating completion of sterilization of the display 120 at operation 1260.

Operations 1245, 1250, 1255 and 1160 may correspond to operations 1045, 1050, 1055 and 1060 described with reference to FIG. 10.

As mentioned above, the display apparatus 100 may determine whether or not the user uses the display apparatus 100, by using the user detector 150. During the time in which the user does not use the display apparatus 100, the display apparatus 100 may sterilize the display 120. Accordingly, the display apparatus 100 may sterilize the display 120, which may be contaminated by the user touch, without the user being exposed to ultraviolet light.

Figure 16:
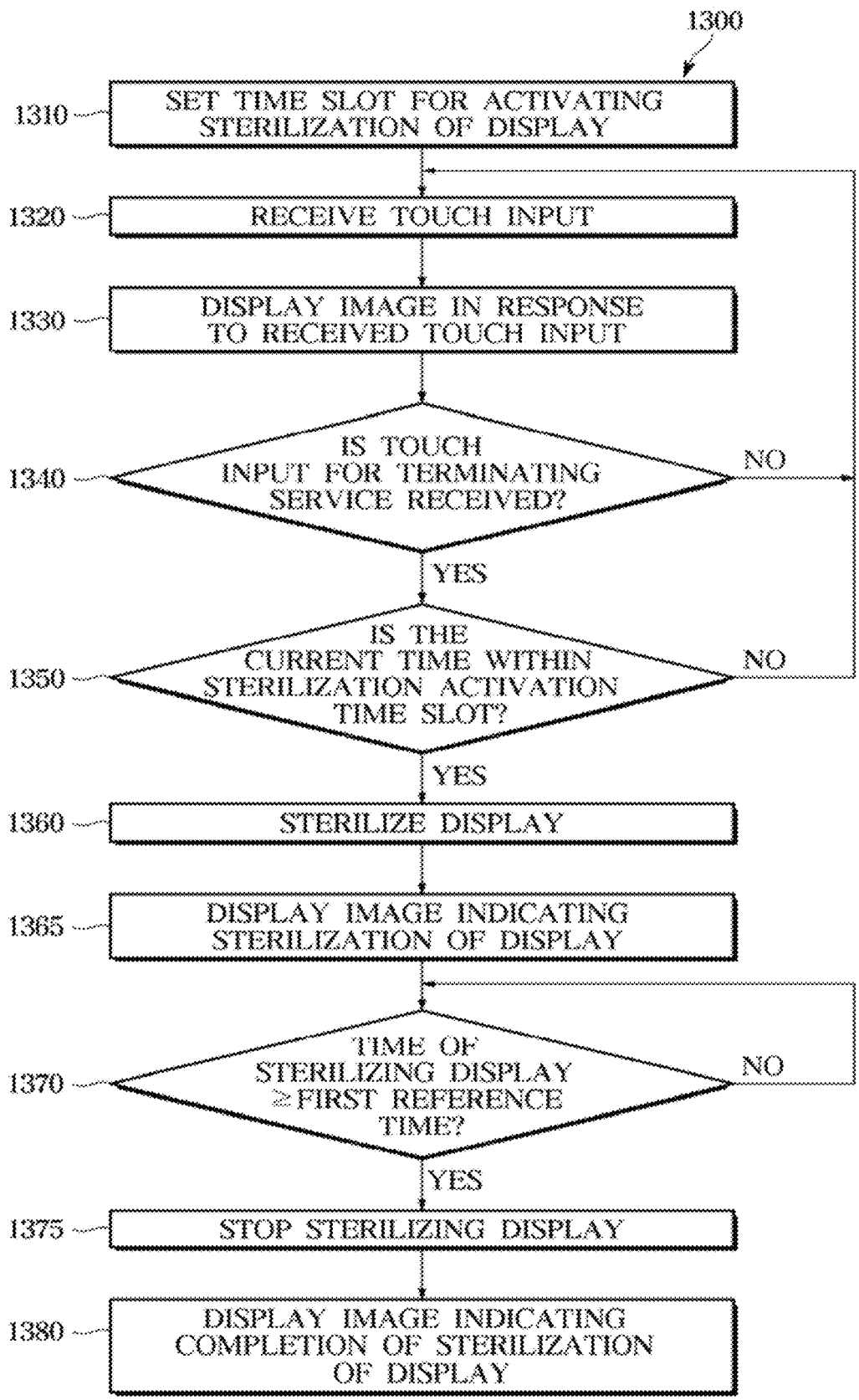
FIG. 16 is a flowchart illustrating another example of the sterilization operation of the display apparatus according to an embodiment.
Figure 17:
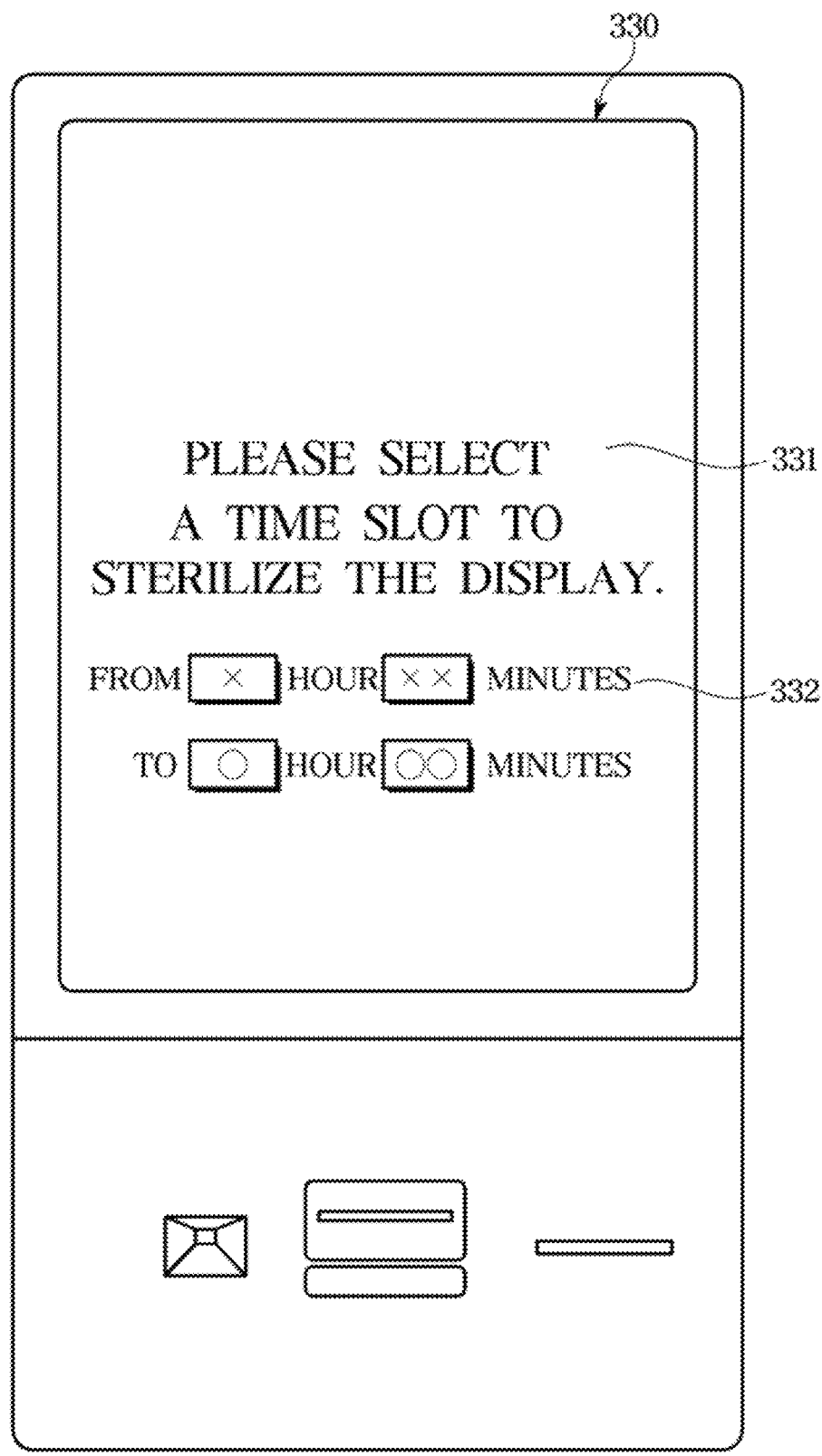
FIG. 17 is a view illustrating an example of an image for setting a sterilization activation time during the sterilization operation of FIG. 16, according to an embodiment.

FIG. 16 is a flowchart illustrating another example of the sterilization operation of the display apparatus according to an embodiment. FIG. 17 is a view illustrating an example of an image for setting a sterilization activation time during the sterilization operation of FIG. 16.

A display sterilization operation 1300 of the display apparatus 100 will be described with reference to FIGS. 16 and 17.

The display apparatus 100 may set a time slot for activating sterilization of the display 120 at operation 1310.

The sterilization of the display 120 may be performed in a sterilization activation time slot that is pre-set. For example, the sterilization of the display 120 may be deactivated during a time slot in which there are many users of the display apparatus 100. The sterilization of the display 120 may be activated during a time slot in which there are few users of the display apparatus 100.

The time slot for activating sterilization of the display 120 may be input by the user. For example, the controller 180 may display a sterilization setting screen 330 on the display 120 as illustrated in FIG. 17.

The sterilization setting screen 330 may include a guide message 331 for selecting a time slot for activating sterilization of the display 120. The sterilization setting screen 330 may include a time slot input area 332 configured to receive a time slot for activating sterilization of the display 120. In the time slot input area 332, the user may input an activation time to activate sterilization of the display 120 and a deactivation time to deactivate sterilization of the display 120.

After the time slot for activating sterilization is set, the display apparatus 100 may receive a touch input from the user at operation 1320. The display apparatus 100 may display an image in response to the user touch input at operation 1330. The display apparatus 100 may determine whether or not a touch input for terminating the service is received at operation 1340.

Operations 1320, 1330, and 1340 may correspond to operations 1010, 1020, and 1030 described with reference to FIG. 10.

The display apparatus 100 may determine whether the current time is within the sterilization activation time slot at operation 1350.

The controller 180 may count the current time and compare the current time with a sterilization activation time. When the current time is less than the sterilization activation time, that is, when the current time has not reached the sterilization activation time, the controller 180 may determine that the current time is not within the sterilization activation time slot.

When the current time is greater than the sterilization activation time, that is, when the current time has passed the sterilization activation time, the controller 180 may compare the current time with the sterilization deactivation time. When the current time is less than the sterilization deactivation time, that is, when the current time has not reached the sterilization deactivation time, the controller 180 may determine that the current time is within the sterilization activation time slot.

When the current time is greater than the sterilization deactivation time, that is, when the current time has passed the sterilization activation time, the controller 180 may determine that the current time is not within the sterilization activation time slot.

When it is determined that the current time is not within the sterilization activation time slot (no at operation 1350), the display apparatus 100 may continue to display an image in response to the user touch input.

When it is determined that the current time is within the sterilization activation time slot (yes at operation 1350), the display apparatus 100 may sterilize the display 120, or begin sterilizing the display 120, at operation 1360.

When the current time is within a preset time period for sterilization of the display 120 and when the service provision of the display apparatus 100 is terminated, the controller 180 may sterilize the display panel 103.

In order to sterilize the surface of the display panel 103, the controller 180 may drive the plurality of UV LEDs 230 installed on the front frame 105 to emit ultraviolet light toward the surface of the display panel 103.

During the sterilization of the display 120, the display apparatus 100 may display an image indicating the sterilization of the display 120 at operation 1365. During the sterilization of the display 120, the display apparatus 100 may determine whether the time of sterilizing the display 120 is equal to or greater than the first reference time at operation 1370. When the time of sterilizing the display 120 is equal to or greater than the first reference time (yes at operation 1370), the display apparatus 100 may stop the sterilization of the display 120 at operation 1375. The display apparatus 100 may display an image indicating completion of sterilization of the display 120 at operation 1380.

Operations 1365, 1370, 1375 and 1380 may correspond to operations 1045, 1050, 1055 and 1060 described with reference to FIG. 10.

As mentioned above, the display apparatus 100 may sterilize the display 120 only in the pre-set time slot. Accordingly, the display apparatus 100 may sterilize the display 120, which may be contaminated by the user touch, without the user waiting for the sterilization of the display 120.

Figure 18:
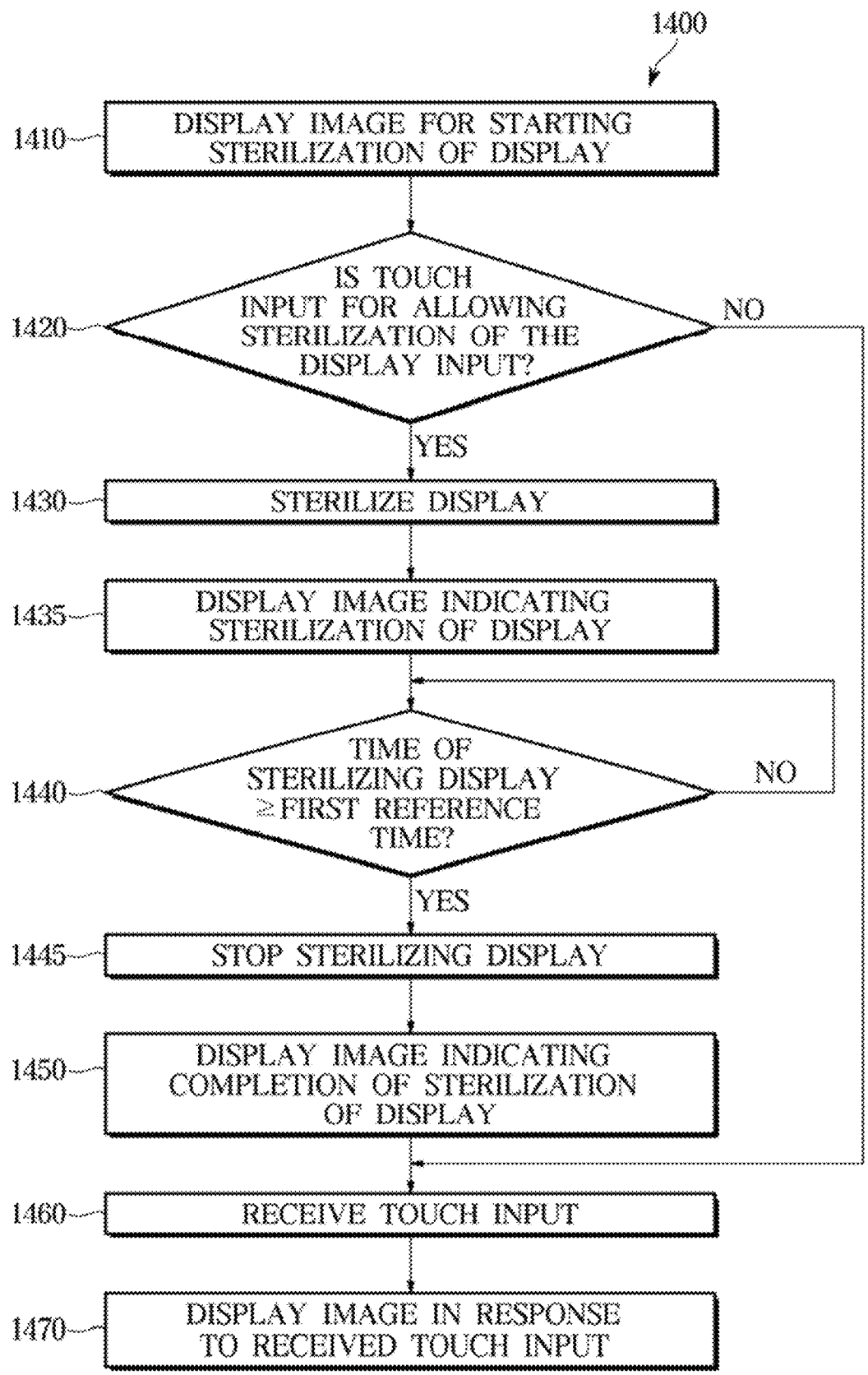
FIG. 18 is a flowchart illustrating another example of the sterilization operation of the display apparatus according to an embodiment.
Figure 19:
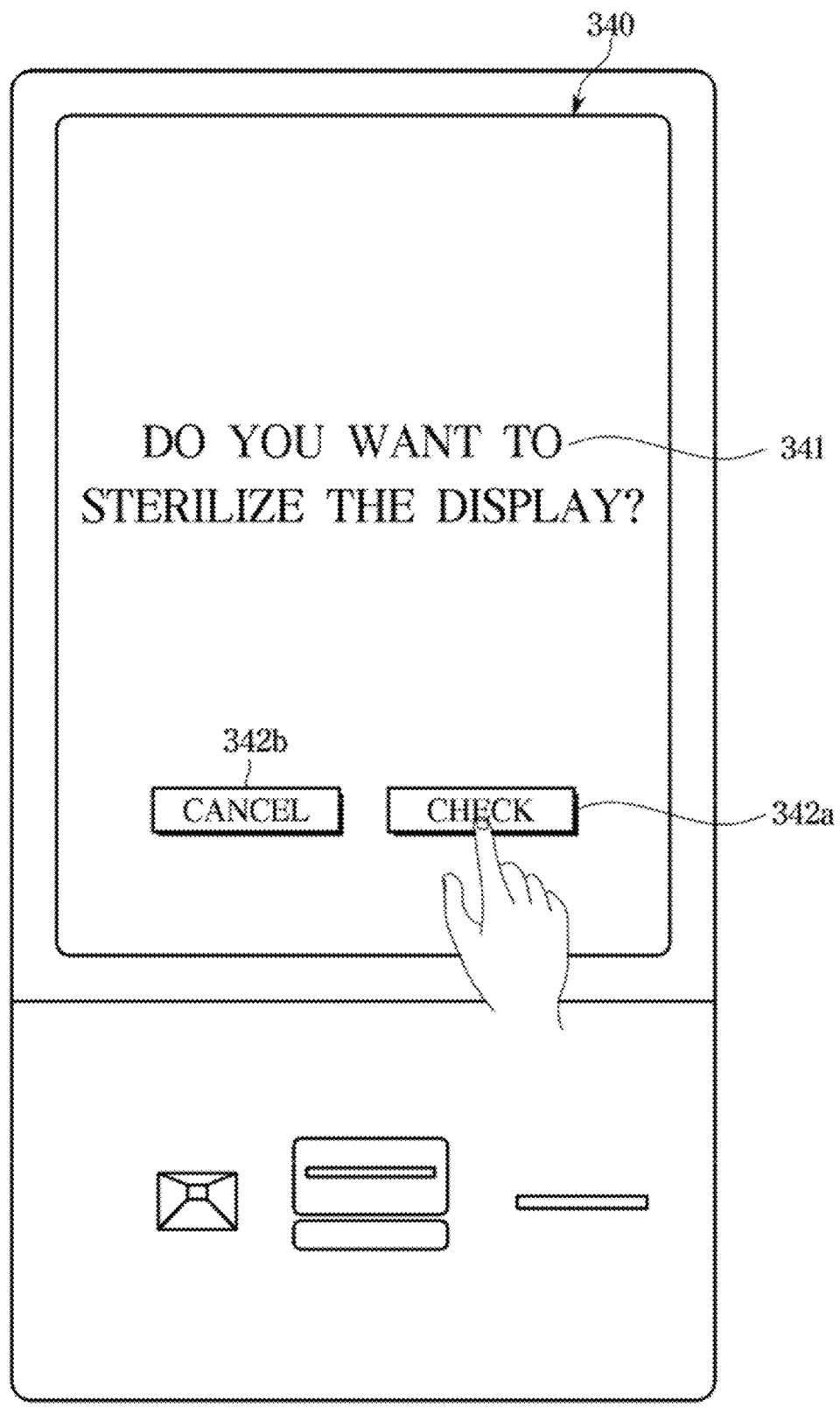
FIG. 19 is a view illustrating an example of an image for starting the sterilization of the display of FIG. 18, according to an embodiment.

FIG. 18 is a flowchart illustrating another example of the sterilization operation of the display apparatus according to an embodiment. FIG. 19 is a view illustrating an example of an image for starting the sterilization of the display of FIG.

A display sterilization operation 1400 of the display apparatus 100 will be described with reference to FIGS. 18 and 19.

The display apparatus 100 displays an image for starting sterilization of the display 120 at operation 1410.

The controller 180 may guide the user to perform sterilization of the display 120 before providing the service to the user. In addition, when the user allows the sterilization of the display 120, the controller 180 may sterilize the display 120 in a state in which the user recognizes sterilization.

For example, the controller 180 may display a sterilization guide screen 340 on the display 120 as illustrated in FIG. 19.

The sterilization guide screen 340 may include a guidance message 341 inducing the user selection as to whether to start the sterilization of the display 120 prior to the provision of the service. The sterilization guide screen 340 may also include a cancel button 342*b* configured to disallow the sterilization of the display 120 and an allow button 342*a* configured to allow the sterilization of the display 120. The user may touch any one of the cancel button 342*b* and the allow button 342*a* of the sterilization guide screen 340 depending on whether or not the user allows to the sterilization of the display 120.

The display apparatus 100 may determine whether or not a touch input for allowing sterilization of the display 120 is input by the user at operation 1420.

The controller 180 may determine whether to sterilize the display 120 in response to a user touch input to the sterilization guide screen 340.

When the allow button 342*a* of the sterilization guide screen 340 is touched by the user, the controller 180 may sterilize the display 120. On the other hand, when the cancel button 342*b* of the sterilization guide screen 340 is touched by the user, the controller 180 may not perform the sterilization of the display 120.

When the touch input allowing the sterilization of the display 120 is received (yes at operation 1420), the display apparatus 100 may sterilize the display 120, or begin sterilizing the display 120, at operation 1430.

When the user allows the sterilization of the display 120 before the provision of the service, the controller 180 may sterilize the display 120 in the state in which the user recognizes sterilization. Therefore, the controller 180 may sterilize the display 120 more safely without emitting ultraviolet light to the user.

In order to sterilize the surface of the display panel 103, the controller 180 may drive the plurality of UV LEDs 230 installed on the front frame 105 to emit ultraviolet light toward the surface of the display panel 103.

During the sterilization of the display 120, the display apparatus 100 may display an image indicating the sterilization of the display 120 at operation 1435. During the sterilization of the display 120, the display apparatus 100 may determine whether the time of sterilizing the display 120 is equal to or greater than the first reference time at operation 1440. When the time of sterilizing the display 120 is equal to or greater than the first reference time (yes at operation 1440), the display apparatus 100 may stop sterilization of the display 120 at operation 1445. The display apparatus 100 may display an image indicating completion of sterilization of the display 120 at operation 1450.

Operations 1435, 1440, 1455 and 1450 may correspond to operations 1045, 1050, 1055 and 1060 described with reference to FIG. 10.

When a touch input disallowing the sterilization of the display 120 is received (no at operation 1420) or when the sterilization of the display 120 is completed, the display apparatus 100 may receive the touch input from the user at operation 1460 and display an image in response to the received touch input on the display 120 at operation 1470.

Operations 1460 and 1470 may correspond to operations 1010 and 1020 described with reference to FIG. 10.

As mentioned above, the display apparatus 100 may guide the sterilization of the display 120 to the user before providing the service, and sterilize the display 120 based on the user selection. Accordingly, the display apparatus 100 may sterilize the display 120, which may be contaminated by the user touch, without the user being exposed to ultraviolet light.

Figure 20:
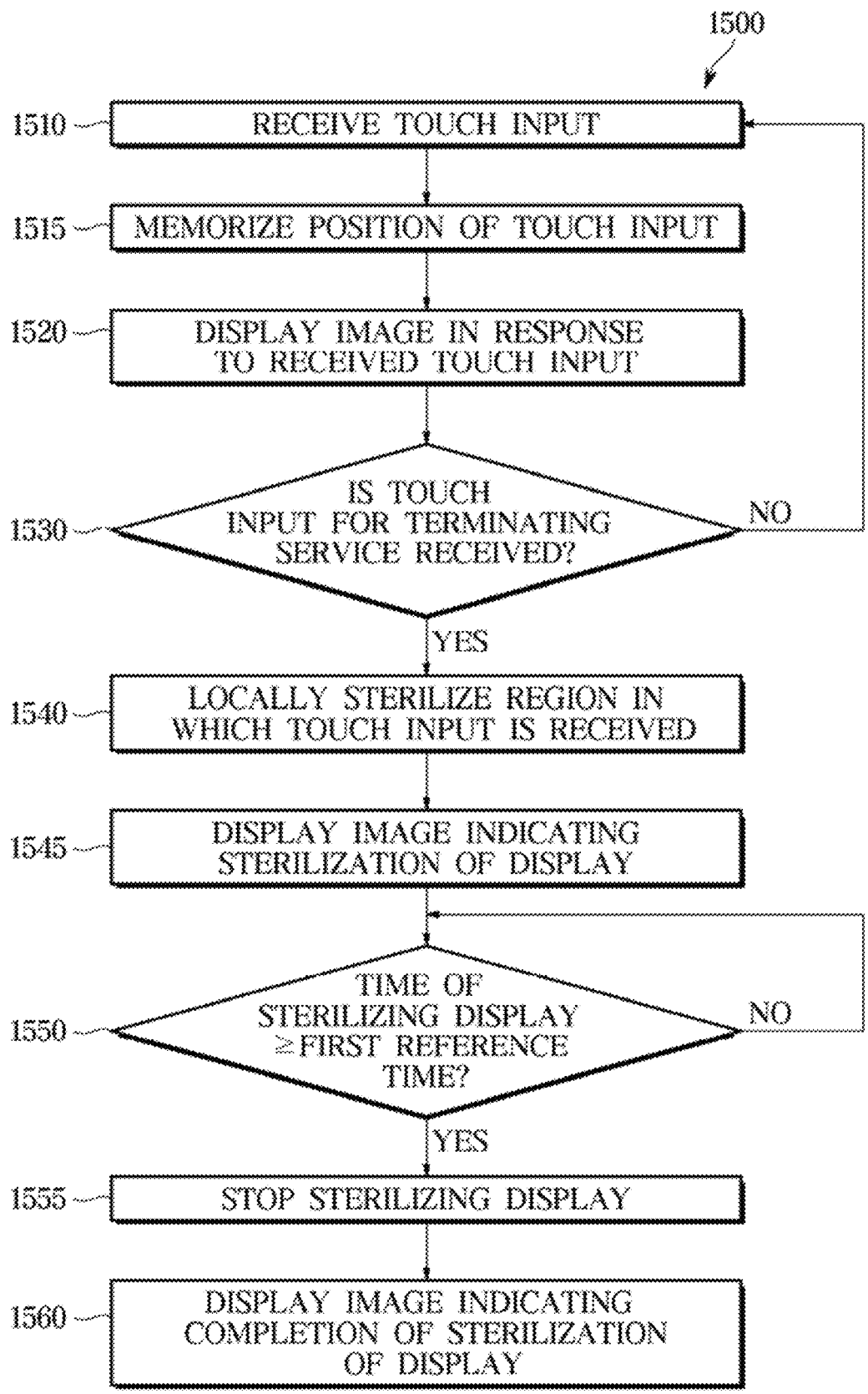
FIG. 20 is a flowchart illustrating another example of the sterilization operation of the display apparatus according to an embodiment.
Figure 21:
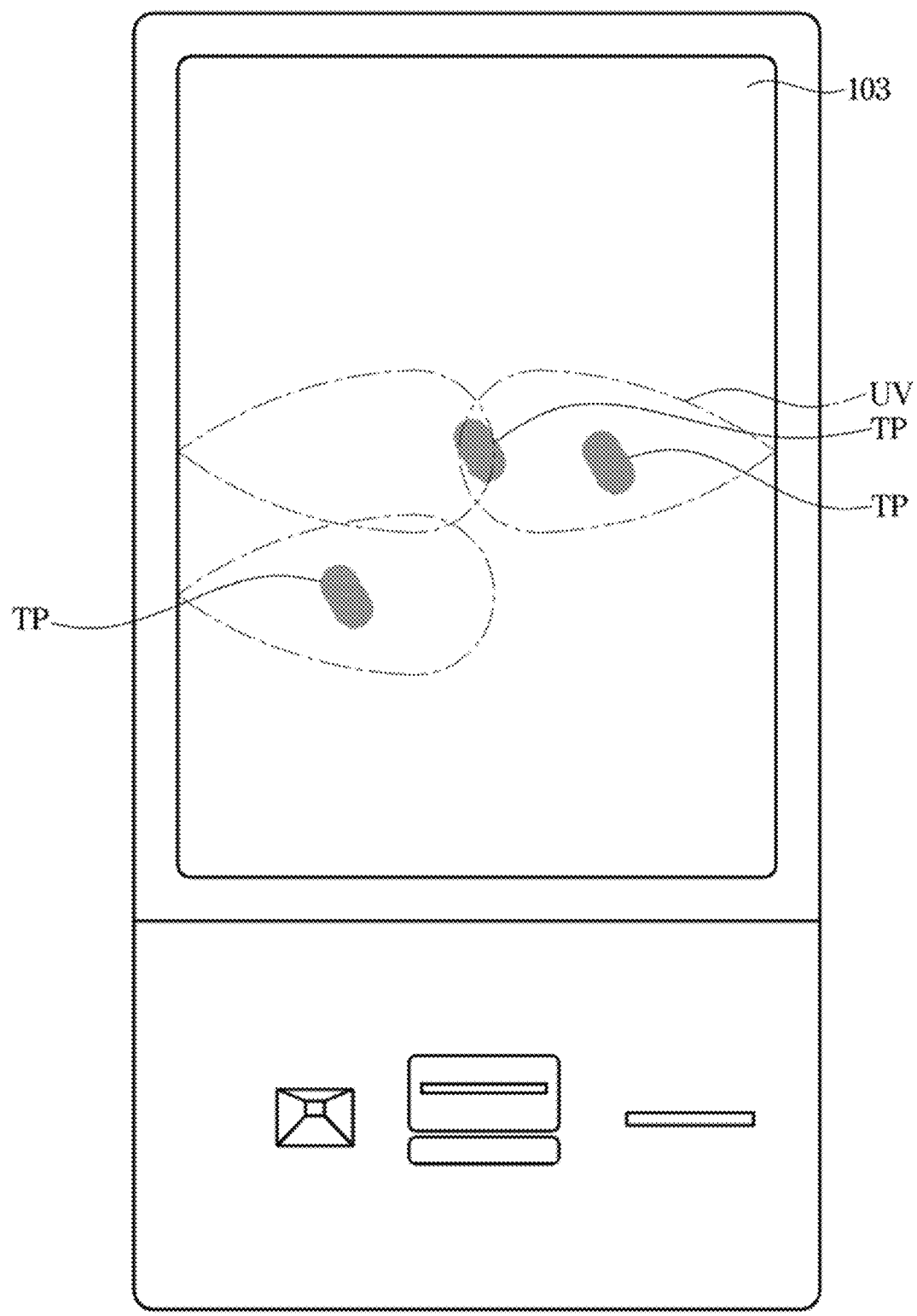
FIG. 21 is view illustrating an example of locally sterilizing the display of FIG. 20, according to an embodiment.

FIG. 20 is a flowchart illustrating another example of the sterilization operation of the display apparatus according to an embodiment. FIG. 21 is view illustrating an example of locally sterilizing the display of FIG. 20.

A display sterilization operation 1500 of the display apparatus 100 will be described with reference to FIGS. 20 and 21.

The display apparatus 100 may receive a touch input from a user at operation 1510.

The controller 180 may display an image inducing the user command or the user selection on the display 120 and receive a user touch input trough the infrared touch frame 110.

Operation 1510 may correspond to operation 1010 described with reference to FIG. 10.

The display apparatus 100 may memorize, or store, a touch position of a user touch input at operation 1515.

The infrared touch frame 110 may detect a user touch and identify a touch position. The controller 180 may receive a user touch position from the infrared touch frame 110 and determine a touch input based on the image of the display 120 and the user touch position.

The controller 180 may separately memorize a user touch position received from the infrared touch frame 110. For example, as illustrated in FIG. 21, the controller 180 may store the position of the user touch points TP.

The display apparatus 100 may display an image in response to the received touch input at operation 1520.

The controller 180 may display an image, which is in response to the touch input obtained through the infrared touch frame 110, on the display 120.

Operation 1520 may correspond to operation 1020 described with reference to FIG. 10.

The display apparatus 100 may determine whether a touch input for terminating the service is received at operation 1530.

The controller 180 may identify whether the user touch input is a touch input indicating termination of the service for the corresponding user based on the image of the display 120 and the user touch input.

Operation 1530 may correspond to operation 1030 described with reference to FIG. 10.

When it is determined that a touch input for terminating the service is not received (no at operation 1530), the display apparatus 100 may receive a user touch input, store a position of the user touch input and display an image in response to the user touch input.

When it is determined that a touch input for terminating the service is received (yes at operation 1530), the display apparatus 100 may locally sterilize the display 120 at operation 1540.

The controller 180 may divide the surface of the display panel 103 into a plurality of sterilization regions based on the position where the plurality of UV LEDs 230 is installed. For example, as illustrated in FIG. 5, when 7 UV LEDs are installed on opposite sides of the display panel 103 that is total 14 UV LEDs are installed in the display panel 103, the controller 180 may divide the surface of the display panel 103 into 14 sterilization regions based on a distance to the plurality of UV LEDs 230.

However, the number of the plurality of sterilization regions is not limited to the number of the plurality of UV LEDs 230. For example, regardless of the number of the plurality of UV LEDs 230, the controller 180 may divide the display panel 103 into a left region and a right region, or divide the display panel 103 into an upper region and a lower region, or divide the display panel 103 into an upper region, a central region, and a lower region.

The controller 180 may determine a sterilization region, in which the touch point TP is located, based on the position of the user touch point TP.

The controller 180 may selectively sterilize a sterilization region, in which a touch point TP is located, among the plurality of sterilization regions. For example, among the plurality of UV LEDs 230, the controller 180 may selectively drive an UV LED configured to emit ultraviolet light to a sterilization region to be sterilized, as illustrated in FIG. 21.

By selectively driving the UV LED, the controller 180 may locally sterilize the display panel 103. The power consumption may be reduced due to this driving of the UV LED. Further, the amount of ultraviolet light emitted from the UV LEDs may be reduced, and thus the amount of ultraviolet light exposed to the user may also be reduced.

During the sterilization of the display 120, the display apparatus 100 may display an image indicating the sterilization of the display 120 at operation 1545. During the sterilization of the display 120, the display apparatus 100 may determine whether the time of sterilizing the display 120 is equal to or greater than the first reference time at operation 1550. When the time of sterilizing the display 120 is equal to or greater than the first reference time (yes at operation 1550), the display apparatus 100 may stop sterilization of the display 120 at operation 1555. The display apparatus 100 may display an image indicating completion of sterilization of the display 120 at operation 1560.

Operations 1545, 1550, 1555, and 1560 may correspond to operations 1045, 1050, 1055, and 1060 described with reference to FIG. 10.

As mentioned above, the display apparatus 100 may store the position of the user touch point (TP), and locally sterilize the display panel 103 based on the position of the user touch point (TP). Accordingly, the power consumption may be reduced due to this driving of the UV LED. Further, the amount of ultraviolet light emitted from the UV LEDs may be reduced, and thus the amount of ultraviolet light exposed to the user may also be reduced.

Figure 22:
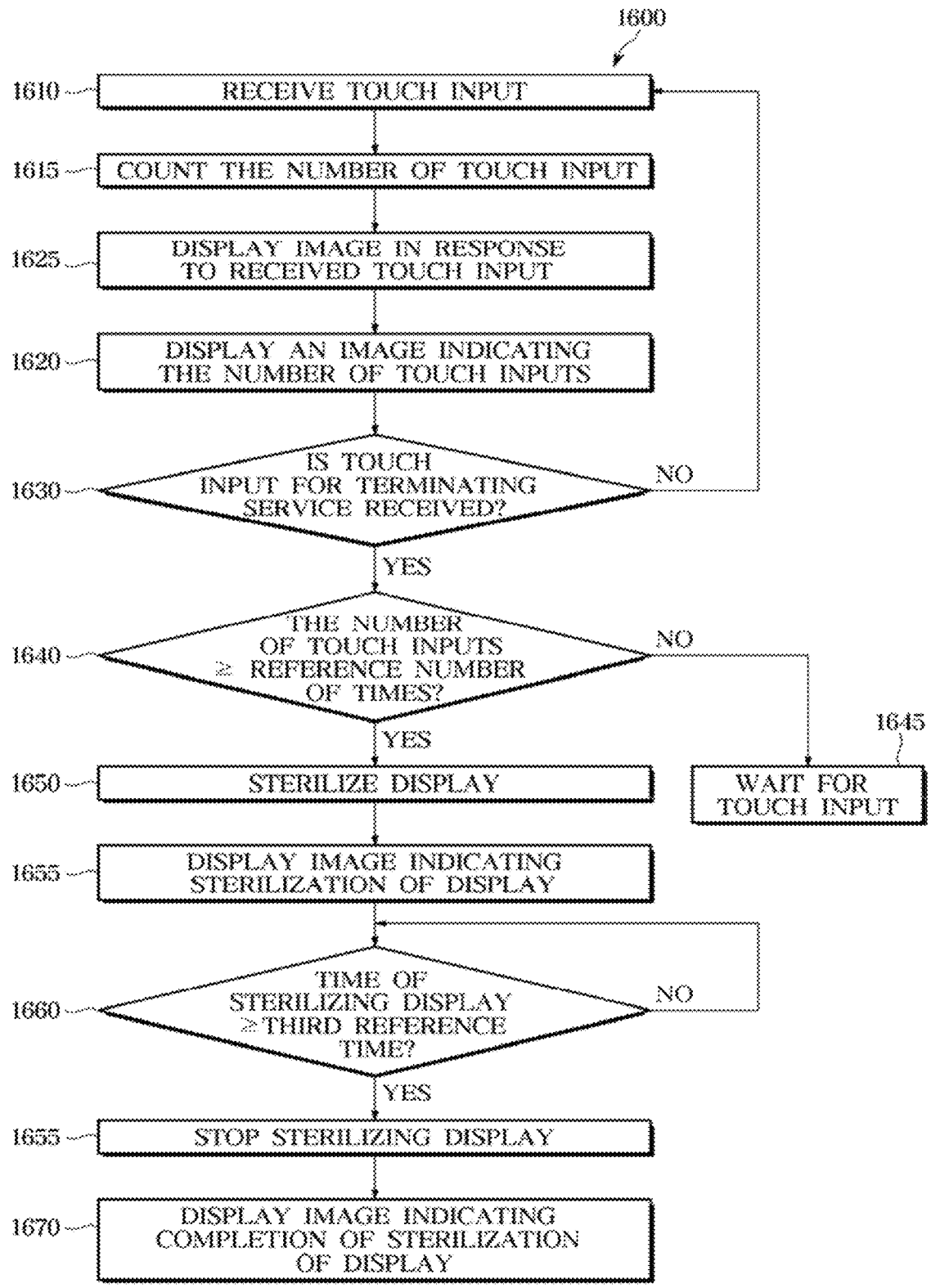
FIG. 22 is a flowchart illustrating another example of the sterilization operation of the display apparatus according to an embodiment.
Figure 23:
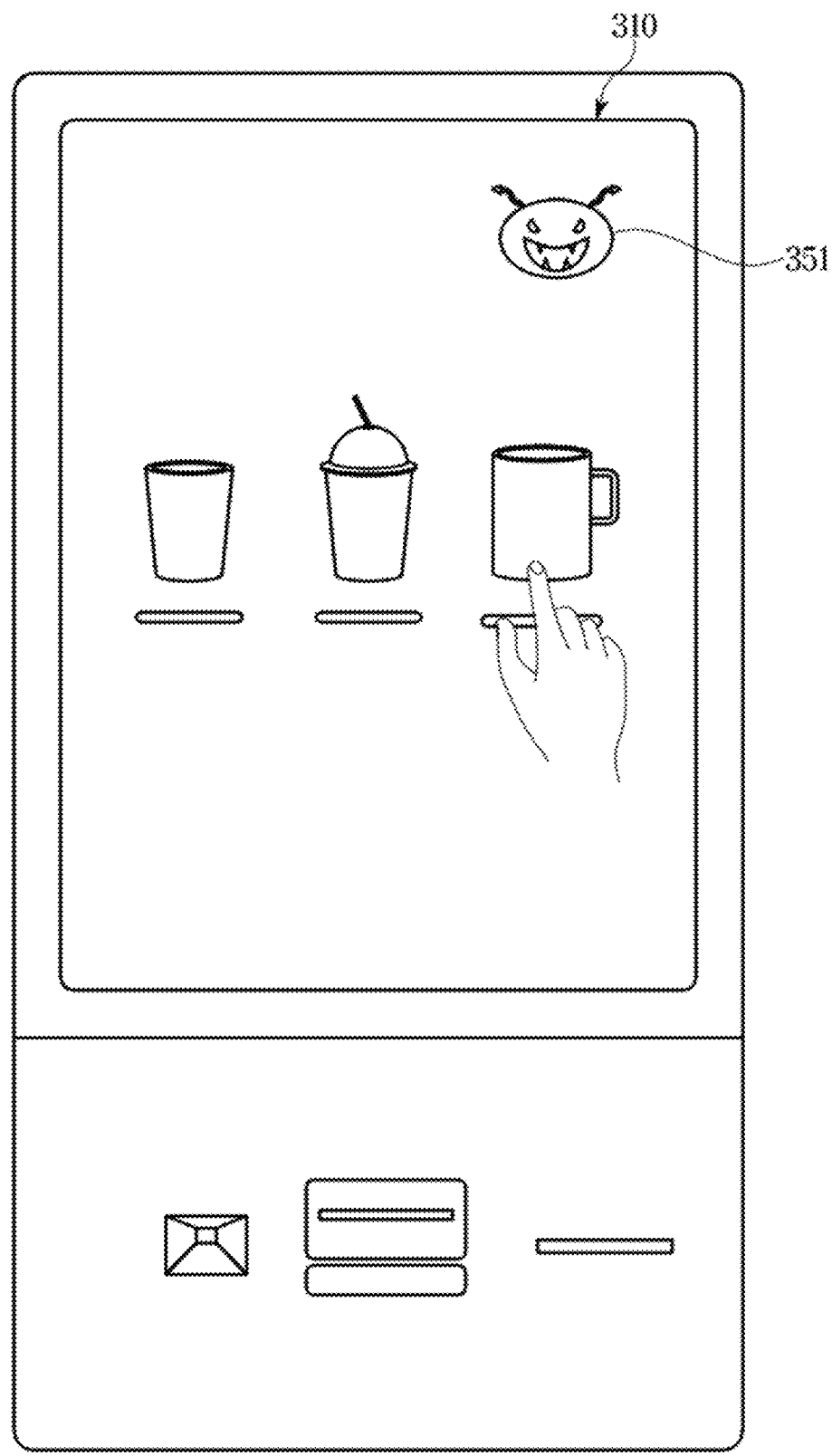
FIG. 23 is a view illustrating an example of an image indicating the number of touch inputs illustrated in FIG. 22, according to an embodiment.

FIG. 22 is a flowchart illustrating another example of the sterilization operation of the display apparatus according to an embodiment. FIG. 23 is a view illustrating an example of an image indicating the number of touch inputs illustrated in FIG. 22.

A display sterilization operation 1600 of the display apparatus 100 will be described with reference to FIGS. 22 and 23.

The display apparatus 100 may receive a touch input from a user at operation 1610.

Operation 1610 may correspond to operation 1010 described with reference to FIG. 10.

The display apparatus 100 may count the number of touch inputs of the user at operation 1615.

The infrared touch frame 110 may detect a user touch and identify a touch position. The controller 180 may receive a user touch position from the infrared touch frame 110.

The controller 180 may receive the user touch position and count the number of times in which the user touches the display 120. Particularly, the controller 180 may count the number of times in which one or more users touched the display 120 after the most recent sterilization of the display 120.

The display apparatus 100 may display an image in response to the received touch input at operation 1620.

Operation 1620 may correspond to operation 1020 described with reference to FIG. 10.

The display apparatus 100 may display an image indicating the number of touch inputs of the user at operation 1625.

The controller 180 may display an image indicating an image in response to the user touch input and an image indicating the number of touch inputs on the display 120.

As illustrated in FIG. 23, the controller 180 may display a screen 350 including a warning image 351 in the shape of bacteria on the display 120 depending on an increase in the number of touch inputs. For example, when the number of touch inputs is greater than or equal to a predetermined threshold number, the controller 180 may display the warning image 351 in the shape of bacteria on the display 120.

The controller 180 may change the color of the warning image 351 depending on an increase in the number of touch inputs. For example, as the number of touch inputs increases, the controller 180 may change the color of the warning image 351 from blue to yellow to red. When the number of touch inputs is small, the controller 180 may display the warning image 351 in blue, and when the number of touch inputs increases, the controller 180 may display the warning image 351 in yellow. In addition, when the number of touch inputs increases and becomes greater than or equal to a reference number of times, the controller 180 may display the warning image 351 in red.

The controller 180 may display a number or a letter indicating the number of touches input on the display 120.

As mentioned above, by displaying the image indicating the number of touch inputs, the display apparatus 100 may make the user aware of the degree of contamination of the display panel 103 and inform the user of the need to sterilize the display panel 103.

The display apparatus 100 may determine whether a touch input for terminating the service is received at operation 1630.

Operation 1630 may correspond to operation 1030 described with reference to FIG. 10.

The display apparatus 100 may determine whether the number of touch inputs is greater than or equal to the reference number of times at operation 1640.

The controller 180 may compare the number of times, in which one or two or more users touch the display 120 after the most recent sterilization of the display 120, with the reference number of times.

The reference number of times may be set experimentally or empirically. For example, the reference number of times may be set based on the average number of touch inputs while providing a service to one user.

When the number of touch inputs is less than the reference number of times (no at operation 1640), the display apparatus 100 may wait for a user touch input at operation 1645.

When the number of touch inputs is less than the reference number of times, the controller 180 may wait for an additional touch input of an existing user or another user touch input without sterilizing the display 120.

As mentioned above, unnecessary sterilization may be prevented by omitting the sterilization of the display 120 in response to the number of touch inputs being greater than the reference number, and power consumption may be reduced due to the omission of the unnecessary sterilization.

When the number of touch inputs is equal to or greater than the reference number of times (yes at operation 1640), the display apparatus 100 may sterilize the display 120, or begin sterilizing the display 120, at operation 1650.

When the number of touch inputs is equal to or greater than the reference number of times, it may be determined that the surface of the display panel 103 is contaminated by the user touch input. Accordingly, the controller 180 may sterilize the display 120, which may be contaminated by the user touch, without the user being exposed to ultraviolet light.

During the sterilization of the display 120, the display apparatus 100 may display an image indicating the sterilization of the display 120 at operation 1655.

Operation 1655 may correspond to operation 1045 described with reference to FIG. 10.

During the sterilization of the display 120, the display apparatus 100 may determine whether the time of sterilizing the display 120 is equal to or greater than a third reference time at operation 1660.

During the sterilization of the display 120, that is, during the drive of the UV light source 141, the controller 180 may count a time of driving the UV light source 141. In addition, the controller 180 may compare the driving time of the UV light source 141 with the third reference time.

The third reference time may be set depending on the number of touch inputs of the user. For example, as the number of touch inputs of a user increases after the most recent sterilizing of the display 120, the third reference time may increase.

By changing the third reference time depending on the number of touch inputs of the user, the display apparatus 100 may effectively sterilize the display 120.

When the time of sterilizing the display 120 is equal to or greater than the third reference time (yes at operation 1660), the display apparatus 100 may stop the sterilization of the display 120 at operation 1665. The display apparatus 100 may also display an image indicating the sterilization of the display 120 at operation 1670.

Operations 1665 and 1670 may correspond to operations 1055 and 1060 described with reference to FIG. 10.

As mentioned above, the display apparatus 100 may sterilize the display 120 depending on the number of the user touch input. By omitting the sterilization of the display 120 depending on the number of touch inputs, unnecessary sterilization may be prevented and power consumption may be reduced due to the omission of the unnecessary sterilization. In addition, by adjusting a sterilization time depending on the number of the user touch input, the display apparatus 100 may effectively sterilize the display 120.

In the above, the display apparatus 100 including the infrared touch frame 110 configured to detect a user touch input using infrared light has been described. However, the display apparatus 100 is not limited to including the infrared touch frame 110. For example, the display apparatus 100 may include a capacitive type touch panel or a resistive film type touch panel to receive a user touch input.

Figure 24:
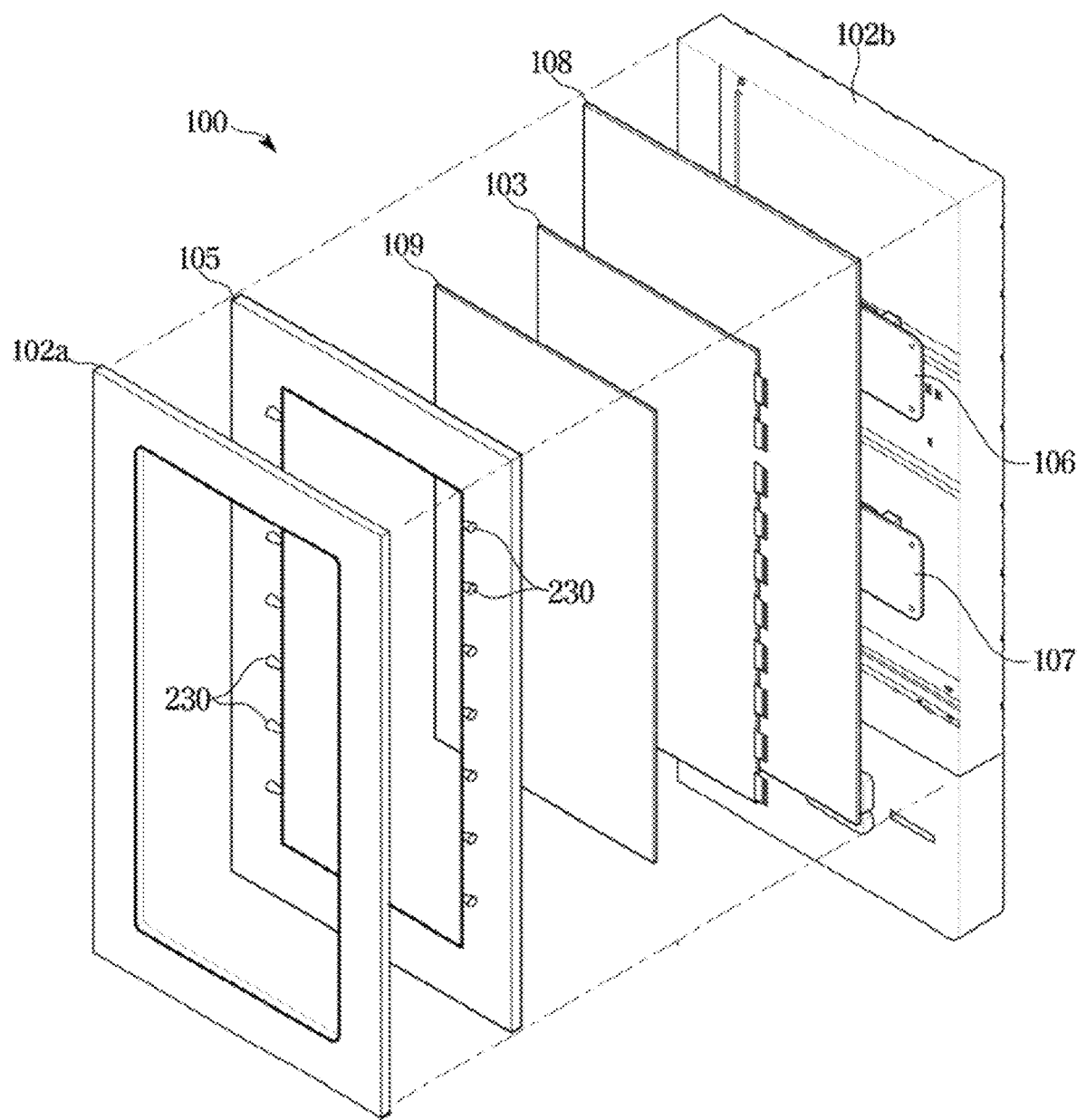
FIG. 24 is a view illustrating another example of the display apparatus according to an embodiment.

FIG. 24 is a view illustrating another example of the display apparatus according to an embodiment.

Referring to FIG. 24, the display apparatus 100 may include a display panel 103 configured to display an image, a touch panel 109 configured to detect a user touch input, and a front frame 105 in which a plurality of UV LEDs 230 is installed.

The display panel 103 may include a LED panel, an inorganic LED panel, or an OLED panel.

The touch panel 109 may include a capacitive type touch panel. For example, the touch panel 109 may include a plurality of electrodes, and may detect a user touch based on a change in capacitance among the plurality of electrodes. In addition, the touch panel 109 may include a resistive film, and may detect a user touch based on a change in the electrical resistance value of the resistive film.

The front frame 105 may be provided with the plurality of UV LEDs 230 for sterilizing the touch panel 109. The touch panel 109 may be contaminated by bacteria by the user touch. The plurality of UV LEDs 230 installed on the front frame 105 may emit ultraviolet light toward the touch panel 109. The plurality of UV LEDs 230 may sterilize the touch panel 109 using ultraviolet light.

The display apparatus 100 may include a control assembly 106 in which a control circuit is mounted, and a power assembly 107 in which a power supply circuit is mounted. The control assembly 106 and the power assembly 107 may be the same as the control assembly and power assembly illustrated in FIG. 3. In addition, the control circuit of the control assembly 106 may perform the same operation as the controller 180 described with reference to FIGS. 1 to 23.

Figure 25:
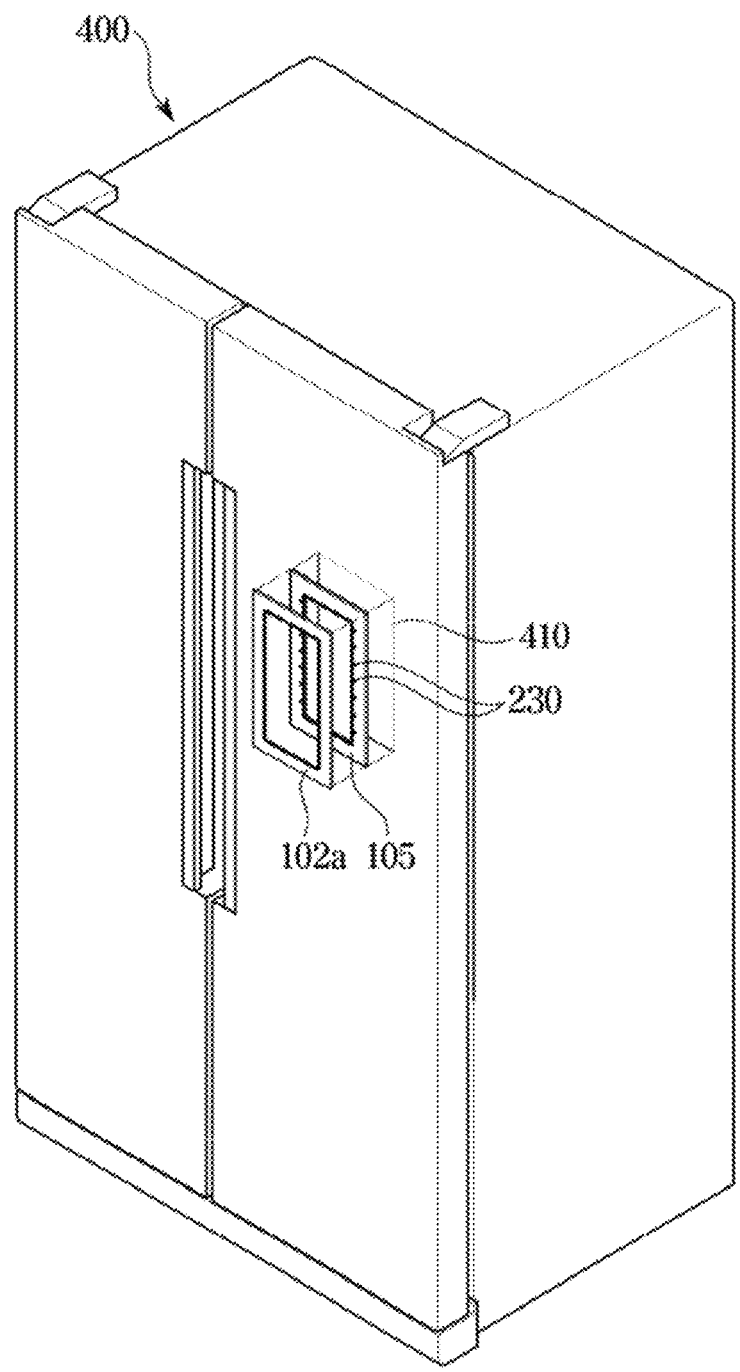
FIG. 25 is a view illustrating a refrigerator including a touch sensitive display according to an embodiment.

FIG. 25 is a view illustrating a refrigerator including a touch sensitive display according to an embodiment.

A refrigerator 400 may include a body in which a storage compartment is formed and a front surface thereof is open, and a door configured to close the open front surface of the body. A touch sensitive display 410 is provided on the door of the refrigerator 400. The touch sensitive display 410 of the refrigerator 400 may receive a touch input of a touch user and display an image in response to the user touch input.

A plurality of UV LEDs 230 configured to sterilize a surface of the touch sensitive display 410 may be provided in front of the touch sensitive display 410.

The plurality of UV LEDs 230 may be installed on the front frame 105, and the front frame 105 may be installed on an edge portion of the touch sensitive display 410. In addition, a front bezel 102a may prevent the plurality of UV LEDs 230 from being exposed to the outside.

After the user uses the touch sensitive display 410, the plurality of UV LEDs 230 may sterilize the touch sensitive display 410 by emitting ultraviolet light toward the touch sensitive display 410.

Figure 26:
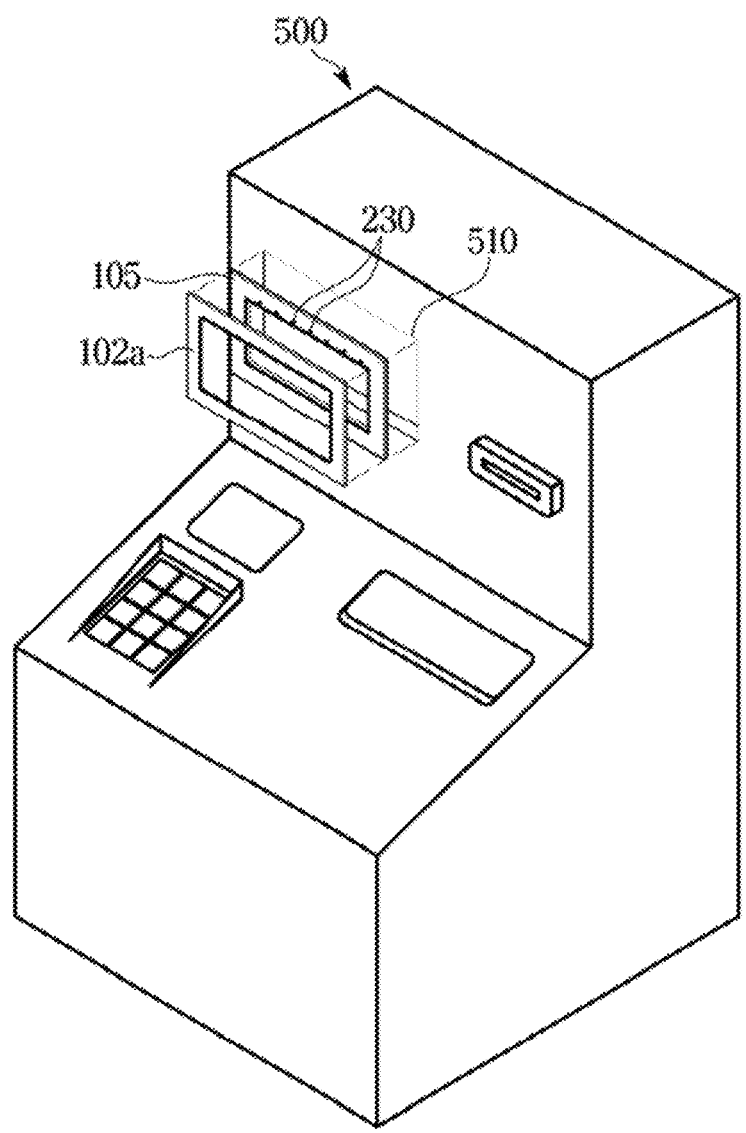
FIG. 26 is a view illustrating an Automated Teller Machine (ATM) including the touch sensitive display according to an embodiment.

FIG. 26 is a view illustrating an Automated Teller Machine (ATM) including a touch sensitive display according to an embodiment.

The ATM 500 may include a body in which cash is stored. A touch sensitive display 510 is provided on the front of the body. The touch sensitive display 510 may receive a touch user touch input and display an image in response to the user touch input.

A plurality of UV LEDs 230 configured to sterilize a surface of the touch sensitive display 510 may be provided in front of the touch sensitive display 510. The plurality of UV LEDs 230 may be installed on a front frame 105, and the plurality of UV LEDs 230 may be prevented from being exposed to the outside by a front bezel 102a.

The plurality of UV LEDs 230 may be installed on an edge portion of the touch sensitive display 510 and particularly may be installed on any one of four edge portions of the touch sensitive display 510 according to the size of the touch sensitive display 510.

After the user uses the touch sensitive display 510, the plurality of UV LEDs 230 may sterilize the touch sensitive display 510 by emitting ultraviolet light toward the touch sensitive display 510.

Figure 27:
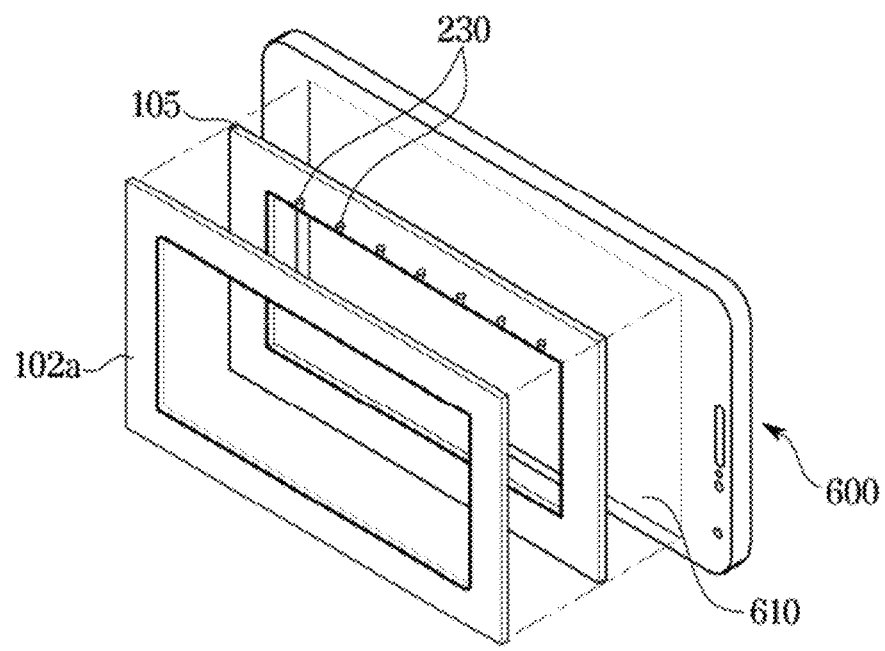
FIG. 27 is a view illustrating a portable multimedia device including the touch sensitive display according to an embodiment.

FIG. 27 is a view illustrating a portable multimedia device including a touch sensitive display according to an embodiment.

The portable multimedia device 600 may include a body having a substantially rectangular flat plate shape. A touch sensitive display 610 configured to receive an image of a user touch and display an image in response to the touch input is provided on the front of the body.

A front frame 105 is provided at an edge portion of the touch sensitive display 610. A plurality of UV LEDs 230 configured to sterilize a surface of the touch sensitive display 610 may be provided on the front frame 105. The plurality of UV LEDs 230 may be prevented from being exposed to the outside by a front bezel 102a.

The plurality of UV LEDs 230 may be installed on any one of four edge portions of the touch sensitive display 610 according to the size of the touch sensitive display 610.

After the user uses the touch sensitive display 610, the plurality of UV LEDs 230 may sterilize the touch sensitive display 610 by emitting ultraviolet light toward the touch sensitive display 610.

As mentioned above, the electronic device may include the touch sensitive display. The plurality of UV LEDs configured to sterilize the touch sensitive display may be installed on the edge portion of the touch sensitive display. The plurality of UV LEDs may sterilize the touch sensitive display after the user has finished using the electronic device.

The display apparatus may include a display panel, a touch sensor provided on the display panel and configured to detect a user touch input, an ultraviolet (UV) light source provided on an edge portion of the display panel and configured to emit ultraviolet light to the display panel from the edge portion of the display panel, and a controller electrically connected to the display panel, the touch sensor, and the UV light source, and configured to allow the UV light source to emit ultraviolet light toward the display panel in response to no user touch input being detected by the touch sensor.

The touch sensor may include an infrared light source provided on one edge portion of the display panel and configured to emit infrared light, and an infrared sensor provided on another edge portion of the display panel and configured to detect infrared light.

Accordingly, the display apparatus may sterilize the display panel by emitting ultraviolet light to the display panel without emitting ultraviolet light to the user's body.

The UV light source may include a plurality of ultraviolet light emitting diodes (UVLEDs) provided on the edge portion of the display panel.

Each of the plurality of UV LEDs may include a light emitting diode (LED) chip configured to emit ultraviolet light, and a lens configured to refract the light emitted from the LED chip, and the lens may have a cylindrical shape having one end of a substantially hemispherical shape.

Each of the plurality of UV LEDs may be arranged in such a way that a central axis of the lens is inclined to face the display panel.

Accordingly, in the UV light source, the main optical axis having the highest intensity of ultraviolet light may face the display panel, and thus the sterilizing effect on the display panel may be improved.

Each of the plurality of UV LEDs may include a light emitting diode (LED) chip configured to emit ultraviolet light; and a lens configured to refract the light emitted from the LED chip, wherein the lens may have a cylindrical shape having a bevel that is substantially obliquely cut.

Each of the plurality of UV LEDs may be arranged in such a way that a central axis of the lens is substantially parallel to a surface of the display panel and the bevel of the lens faces the display panel.

Accordingly, in the UV light source, the main optical axis having the highest intensity of ultraviolet light may face the display panel, and thus the sterilizing effect on the display panel may be improved.

The display apparatus may further include a front frame installed at the edge portion of the display panel, and the infrared light source may include a plurality of infrared light emitting diodes (IR LEDs) disposed on the front frame. The infrared sensor may include a plurality of infrared photodiodes disposed on the front frame. The UV light source may include the plurality of ultraviolet light emitting diodes (UV LEDs) disposed on the plurality of infrared light emitting diodes or on the plurality of infrared photodiodes.

Accordingly, the plurality of ultraviolet LED may emit ultraviolet light toward the display panel without interfering with the plurality of IR LEDs or the plurality of infrared photodiodes.

The display apparatus may further include a front frame installed at the edge portion of the display panel, and the infrared light source may include a plurality of infrared light emitting diodes (IR LEDs) disposed on the front frame. The infrared sensor may include a plurality of infrared photodiodes disposed on the front frame. The UV light source may include the plurality of ultraviolet light emitting diodes (UV LEDs) disposed between the plurality of IR LEDs or between the plurality of infrared photodiodes.

Accordingly, a thickness of a bezel in which the plurality of UV LEDs and the plurality of infrared light emitting or photodiodes are installed may be minimized.

The controller may control the UV light source to emit ultraviolet light toward the display panel in response to a touch input for terminating a service for a user.

It may be determined that the touch input will be not received for a certain time due to the touch input for terminating the service for the user. Therefore, the display apparatus may sterilize the display panel by emitting ultraviolet light to the display panel without emitting ultraviolet light to the user's body.

The controller may control the UV light source to emit ultraviolet light toward the display panel in response to no touch input being detected by the touch sensor for a reference time after receiving a touch input for terminating a service for a user.

It may be determined that the touch input will be not received for a certain time due to the touch input for terminating the service for the user. Therefore, the display apparatus may sterilize the display panel by emitting ultraviolet light to the display panel without emitting ultraviolet light to the user's body.

It may be determined that there is no additional user waiting a service of the display apparatus based on that the touch input is not received for a certain time after the touch input for terminating the service for the user. Therefore, the display apparatus may sterilize the display panel by emitting ultraviolet light to the display panel without emitting ultraviolet light to the user's body.

The controller may control the UV light source to emit ultraviolet light toward the display panel in response to a touch input for terminating a service for a user and a current time being within a preset sterilization time slot.

Accordingly, the display apparatus may sterilize the display panel without having the user wait for sterilization of the display panel.

The controller may control the UV light source to emit ultraviolet light toward the display panel in response to receiving a touch input allowing sterilization of the display panel from a user.

Accordingly, the display apparatus may allow the user to recognize the sterilization of the display panel, and also prevent the user from touching the display panel during the sterilization of the display panel.

The controller may control the UV light source to locally emit ultraviolet light toward a touch position of a user touch input.

Accordingly, the display apparatus may reduce the amount of ultraviolet radiation, thereby reducing power consumption, and may also reduce the amount of ultraviolet light exposed to the user.

The controller may control the UV light source to emit ultraviolet light toward the display panel based on whether the number of a user touch input is equal to or greater than a reference number.

Accordingly, the display apparatus may prevent unnecessary radiation of ultraviolet light, and may also reduce the amount of ultraviolet light exposed to the user.

The controller may control the UV light source to emit ultraviolet light toward the display panel for a time that depends on the number of a user touch input.

Accordingly, the display apparatus may reduce the amount of ultraviolet radiation, thereby reducing power consumption, and may also reduce the amount of ultraviolet light exposed to the user.

The control method for a display apparatus including a touch sensitive display may include displaying an image on the touch sensitive display, detecting a user touch on the touch sensitive display, emitting ultraviolet light toward the touch sensitive display in response to no touch being detected for a reference time after a user touch is detected, and displaying a predetermined image on the touch sensitive display during emitting ultraviolet light.

As is apparent from the above description, the display apparatus may sterilize the surface of the display in contact with a user's body.

Further, the display apparatus may emit ultraviolet light to the surface of the display without a user being exposed to ultraviolet light.

Although a few embodiments of the present disclosure have been shown and described, it would be appreciated by those skilled in the art that changes may be made in these embodiments without departing from the principles and spirit of the disclosure, the scope of which is defined in the claims and their equivalents.

Exemplary embodiments of the present disclosure have been described above. In the exemplary embodiments described above, some components may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

Accordingly, and in addition to the above described exemplary embodiments, embodiments can thus be implemented through computer readable code/instructions in/on a medium, e.g., a computer readable medium, to control at least one processing element to implement any above described exemplary embodiment. The medium can correspond to any medium/media permitting the storing and/or transmission of the computer readable code.

The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the claims.

What is claimed is:

1. A display apparatus comprising:
a display panel;
a touch sensor provided on the display panel and configured to detect a user touch input;
an ultraviolet (UV) light source provided on an edge portion of the display panel and configured to emit UV light to the display panel from the edge portion of the display panel; and
at least one processor configured to, based on no user touch input being detected for a reference amount of time, control the UV light source to emit the UV light toward the display panel, and control the display panel to display a predetermined image indicating that the display panel is being sterilized while emitting the ultraviolet light.

2. The display apparatus of claim 1, wherein the touch sensor comprises:
an infrared light source provided on a first edge portion of the display panel and configured to emit infrared light, and
an infrared sensor provided on a second edge portion of the display panel and configured to detect the infrared light.

3. The display apparatus of claim 1, wherein the UV light source comprises a plurality of UV light emitting diodes (UV LEDs) provided on the edge portion of the display panel.

4. The display apparatus of claim 3, wherein each of the plurality of UV LEDs comprises:
an LED chip configured to emit the UV light; and
a lens configured to refract the UV light emitted from the LED chip,
wherein the lens has a cylindrical shape, and
wherein one end of the cylindrical shape has a substantially hemispherical shape.

5. The display apparatus of claim 4, wherein a central axis of the lens is inclined to face the display panel.

6. A display apparatus comprising:
a display panel;
a touch sensor provided on the display panel and configured to detect a user touch input an ultraviolet (UV) light source provided on an edge portion of the display panel and configured to emit UV light to the display panel from the edge portion of the display panel; and at least one processor configured to, based on no user touch input being detected for a reference amount of time, control the UV light source to emit the UV light toward the display panel, wherein the UV light source comprises a plurality of UV light emitting diodes (UV LEDs) provided on the edge portion of the display panel, and wherein each of the plurality of UV LEDs comprises:

an LED chip configured to emit the UV light; and a lens configured to refract the UV light emitted from the LED chip, wherein the lens has a cylindrical shape having a bevel that is substantially oblique.

7. The display apparatus of claim 6, wherein a central axis of the lens is substantially parallel to a surface of the display panel and, wherein the bevel of the lens faces the display panel.

8. The display apparatus of claim 1, wherein the at least one processor is further configured to control the UV light source to emit the UV light toward the display panel based on a touch input for terminating a service.

9. The display apparatus of claim 1, wherein the at least one processor is further configured to control the UV light source to emit the UV light toward the display panel based on a determination that the user touch input is not detected for the reference amount of time after receiving a touch input for terminating a service.

10. The display apparatus of claim 1, wherein the at least one processor is further configured to control the UV light source to emit the UV light toward the display panel based on a touch input for terminating a service while a current time is within a predetermined sterilization time slot.

11. The display apparatus of claim 1, wherein the at least one processor is further configured to control the UV light source to emit the UV light toward the display panel based on a touch input allowing sterilization of the display panel.

12. The display apparatus of claim 1, wherein the at least one processor is further configured to control the UV light source to emit the UV light toward a touch position corresponding to the user touch input.

13. The display apparatus of claim 1, wherein the at least one processor is further configured to determine a number of times that the user touch input is received, and to control the UV light source to emit the UV light toward the display panel based on whether the number is equal to or greater than a reference number.

14. The display apparatus of claim 1, wherein the at least one processor is further configured to control the UV light source to emit the UV light toward the display panel for an amount of time that determined based on a number of times that the user touch input is received.

15. A control method for a display apparatus including a touch sensitive display, the control method comprising:

displaying an image on the touch sensitive display;

detecting a user touch on the touch sensitive display;

based on no user touch being detected for a reference amount of time, emitting ultraviolet light toward the touch sensitive display; and displaying a predetermined image indicating that the display panel is being sterilized on the touch sensitive display while emitting the ultraviolet light.

16. The control method of claim 15, wherein the ultraviolet light is emitted toward the touch sensitive display based on a touch input for terminating a service.

17. The control method of claim 15, wherein the ultraviolet light is emitted toward the touch sensitive display based on a determination that the user touch is not detected by the touch sensitive display for the reference time after receiving a touch input for terminating a service.

18. The control method of claim 15, wherein the ultraviolet light is emitted toward the touch sensitive display based on a touch input for terminating a service while a current time is within a predetermined sterilization time slot.

19. The control method of claim 15, wherein the ultraviolet light is emitted toward a touch position of the user touch.

20. The control method of claim 15, wherein the ultraviolet light is emitted toward the touch sensitive display based on whether a number of times that the user touch is received is equal to or greater than a reference number.

* * * * *